US011543785B2

(12) United States Patent
Shiraki et al.

(10) Patent No.: US 11,543,785 B2
(45) Date of Patent: Jan. 3, 2023

(54) INDUSTRIAL MACHINE STARTUP CONTROL SYSTEM, STARTUP CONTROL METHOD, AND PROGRAM

(71) Applicant: SINTOKOGIO, LTD., Nagoya (JP)

(72) Inventors: Masataka Shiraki, Toyokawa (JP); Yoshiaki Okada, Toyokawa (JP)

(73) Assignee: SINTOKOGIO, LTD., Nagoya (JP)

( * ) Notice: Subject to any disclaimer, the term of this patent is extended or adjusted under 35 U.S.C. 154(b) by 319 days.

(21) Appl. No.: 16/763,258

(22) PCT Filed: Oct. 31, 2018

(86) PCT No.: PCT/JP2018/040442
§ 371 (c)(1),
(2) Date: May 12, 2020

(87) PCT Pub. No.: WO2019/111600
PCT Pub. Date: Jun. 13, 2019

(65) Prior Publication Data
US 2021/0173354 A1 Jun. 10, 2021

(30) Foreign Application Priority Data

Dec. 6, 2017 (JP) .............................. JP2017-233861
Mar. 22, 2018 (JP) .............................. JP2018-053961

(51) Int. Cl.
*G16H 40/60* (2018.01)
*G05B 9/02* (2006.01)
(Continued)

(52) U.S. Cl.
CPC ............ *G05B 9/02* (2013.01); *A61B 5/02055* (2013.01); *A61B 5/1032* (2013.01); *A61B 5/741* (2013.01);
(Continued)

(58) Field of Classification Search
None
See application file for complete search history.

(56) References Cited

U.S. PATENT DOCUMENTS 7,027,621 B1* 4/2006 Prokoski .............. G06V 40/165
340/576
7,227,472 B1* 6/2007 Roe ........................ B60K 28/06
340/576
(Continued)

FOREIGN PATENT DOCUMENTS

JP H10-166192 A 6/1998
JP 2000-271090 A 10/2000
(Continued)

OTHER PUBLICATIONS

Jan. 15, 2019 International Search Report issued in International Patent Application No. PCT/JP2018/040442.
(Continued)

*Primary Examiner* — John A Pauls
(74) *Attorney, Agent, or Firm* — Oliff PLC

(57) ABSTRACT

An industrial machine startup control system for controlling startup of an industrial machine, the industrial machine startup control system including: a vital data measurement device that measures vital data of a worker; a health state analysis device that acquires the vital data of the worker measured by the vital data measurement device, and that determines a health state of the worker based on the acquired vital data; and a startup control device that controls whether or not to allow startup of the industrial machine based on the determination result from the health state analysis device.

14 Claims, 18 Drawing Sheets

(51) Int. Cl.
*A61B 5/0205* (2006.01)
*A61B 5/103* (2006.01)
*A61B 5/00* (2006.01)
*G06V 40/16* (2022.01)
*A61B 5/021* (2006.01)
*A61B 5/024* (2006.01)

(52) U.S. Cl.
CPC ........... *G06V 40/174* (2022.01); *G16H 40/60* (2018.01); *A61B 5/021* (2013.01); *A61B 5/024* (2013.01); *A61B 2503/20* (2013.01)

(56) References Cited

U.S. PATENT DOCUMENTS

| | | | |
|---|---|---|---|
| 2001/0039372 A1 | 11/2001 | Yasushi et al. | |
| 2004/0158430 A1* | 8/2004 | Ballard, Jr. | B60K 28/063 702/183 |
| 2005/0224034 A1* | 10/2005 | Janisch | F02N 11/101 123/179.2 |
| 2013/0151027 A1* | 6/2013 | Petrucci | B60R 16/037 701/1 |
| 2015/0112606 A1* | 4/2015 | He | A61B 5/02055 702/19 |
| 2016/0278644 A1* | 9/2016 | He | A61B 5/7275 |
| 2017/0147958 A1* | 5/2017 | Hatfield | G06Q 10/063114 |
| 2019/0053715 A1* | 2/2019 | Nakamura | A61B 5/6814 |
| 2019/0318284 A1* | 10/2019 | Outram | G06F 16/122 |

FOREIGN PATENT DOCUMENTS

| | | |
|---|---|---|
| JP | 2001-258858 A | 9/2001 |
| JP | 2006-302206 A | 11/2006 |
| JP | 2008-100247 A | 5/2008 |
| JP | 2009-172181 A | 8/2009 |
| JP | 2009-233042 A | 10/2009 |
| JP | 2011-76531 A | 4/2011 |

OTHER PUBLICATIONS

Translation of Jun. 15, 2021 Office Action issued in Japanese Patent Application No. 2018-053961.

* cited by examiner

FIG. 22

| STARTUP SAFETY CHECKLIST | 17/09/28 08:57 |

1. HOW ARE YOU FEELING? — WELL / ILL
2. ARE YOU WEARING DESIGNATED PROTECTIVE GEAR SUCH AS PROTECTIVE GLASSES? — YES / NO
3. IS THERE ANYONE ELSE IN THE MACHINERY OR SURROUNDING DANGER ZONES? — NO / YES
4. IS THE DOOR CLOSED FOR CERTAIN? — CLOSED / OPEN
5. IS THE PROTECTIVE COVER ATTACHED? — ATTACHED / NOT ATTACHED
6. IS THE LID OPEN? — CLOSED / OPEN
7. ARE ANY PROTECTIVE DEVICES OR SENSORS MALFUNCTIONING? — FUNCTIONING / MAL-FUNCTIONING

COMPLETED

116

INDUSTRIAL MACHINE STARTUP CONTROL SYSTEM, STARTUP CONTROL METHOD, AND PROGRAM

TECHNICAL FIELD

The present invention relates to an industrial machine startup control system, a startup control method, and a program.

BACKGROUND

Generally, when starting industrial machines including construction machines, agricultural machines, machine tools, woodworking machines, and the like, it is necessary for conditions, such as all of the actuators being at their origin positions, no one being within the machine driving range, sufficient raw materials being loaded, and the like, to be met.

For example, Patent Document 1 proposes technology wherein a plurality of light emitters and a plurality of light receivers are arranged to form a curtain comprising a plurality of light beams, the presence or absence of workers or materials is detected on the basis of whether the curtain of light beams is blocked, the working state of a worker is determined by counting the number of times, after the curtain of light beams has been blocked, that the blocked light enters a restored state, and an industrial machine is controlled so as to be able to start at a correct timing in accordance with the determination result.

When a worker having a health problem operates an industrial machine, there is a possibility that the health state of the worker will deteriorate during the operating work, and the worker cannot continue to perform the operations. As technology for monitoring the health state of a worker, Patent Document 2 proposes, for example, technology wherein the worker wears a biosensor device that is in a wearable form, and when the biosensor device detects an abnormality in the worker, a warning is displayed in accordance with the type of abnormality.

CITATION LIST

Patent Literature

Patent Document 1: JP H10-166192 A
Patent Document 2: JP 2011-76531 A

SUMMARY OF INVENTION

Technical Problem

However, even with the technology in the above-mentioned Patent Document 2, when a problem arises in the health state of a worker during operating work, the industrial machine must be stopped, and there is a problem in that, not only does it become impossible to operate the industrial machine as planned, but also, there is a risk that the industrial machine will be damaged due to the industrial machine being suddenly stopped or the like.

Therefore, an objective of the present invention is to control the startup of an industrial machine in accordance with the health state of a worker.

Solution to Problem

The industrial machine startup control system according to the present invention is an industrial machine startup control system for controlling startup of an industrial machine, the industrial machine startup control system comprising a vital data measurement device that measures vital data of a worker; a health state analysis device that acquires the vital data of the worker measured by the vital data measurement device, and that determines a health state of the worker based on the acquired vital data; and a startup control device that controls whether or not to allow startup of the industrial machine based on the determination result from the health state analysis device.

The startup control method according to the present invention is a startup control method for controlling startup of an industrial machine, the startup control method comprising a step of measuring vital data of a worker by using a vital data measurement device; a step of determining a health state of the worker, by using a health state analysis device, based on the vital data of the worker, measured by the vital data measurement device; and a step of controlling whether or not to allow startup of the industrial machine, by using a startup control device, based on a determination result from the health state analysis device.

The program according to the present invention makes a computer implement a control function for controlling whether or not to allow startup of an industrial machine based on a health state determined based on vital data of a worker who is to operate the industrial machine.

Advantageous Effects of Invention

According to the present invention, it is possible to control the startup of an industrial machine in accordance with the health state of a worker.

BRIEF DESCRIPTION OF DRAWINGS

FIG. 22 is a schematic view illustrating a display screen on the industrial machine control device 50 according to the present first embodiment.

DESCRIPTION OF EMBODIMENTS

Hereinafter, embodiments of the present invention will be explained with reference to the drawings.

A. First Embodiment

Figure 1:
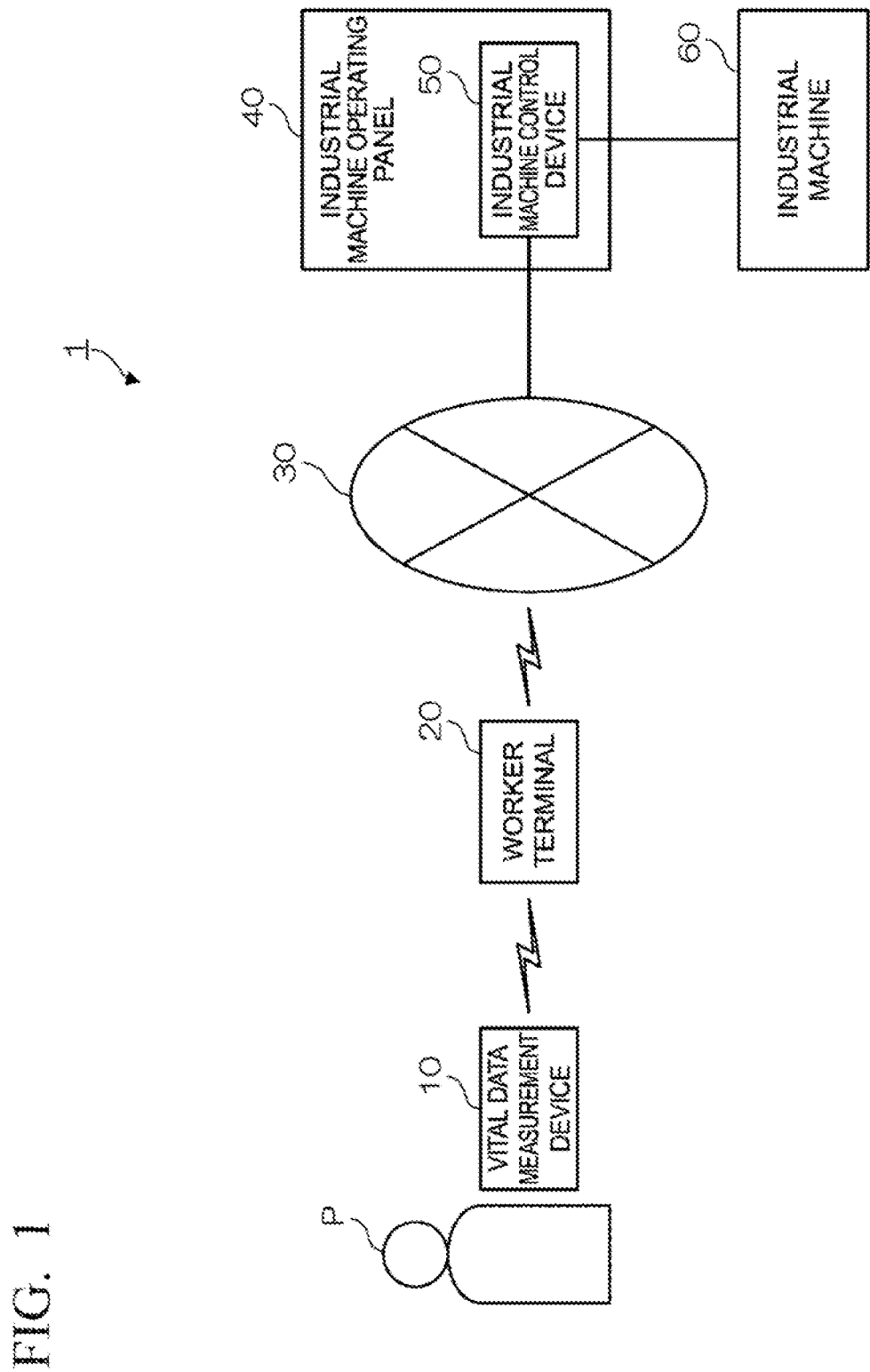
FIG. 1 is a block diagram illustrating the structure of an industrial machine startup control system 1 according to a first embodiment of the present invention.

FIG. 1 is a block diagram illustrating the structure of an industrial machine startup control system 1 according to a first embodiment of the present invention. In FIG. 1, the industrial machine startup control system 1 is composed of a vital data measurement device 10, a worker terminal 20, a network 30, an industrial machine operating panel 40, an industrial machine control device 50, and an industrial machine 60. The vital data measurement device 10 measures vital data (blood pressure, heart rate, body temperature, breath (presence or absence of alcohol), activity level (number of paces), and the like) of a worker P. The vital data measurement device 10 is connected to the worker terminal 20 by cable or wireless (for example, Bluetooth (registered trademark)). The vital data measurement device 10 is not limited to being a single device, and may be composed of a plurality of devices in accordance with the type of vital data.

The measurement results from the vital data measurement device 10 are used to control whether the industrial machine control device 50 will or will not allow startup of the industrial machine 60 as will be explained below. In other words, the vital data measurement device 10 measures the vital data of the worker P at least before the worker P performs work using the industrial machine 60.

The worker terminal (health state analysis device) 20 collects the measured vital data from the vital data measurement device 10 by cable or wireless. The worker terminal 20 is an information processing device (a stand-alone computer or a portable computer, tablet, smartphone, or the like, on which a central processing unit, a memory, and the like are installed) that is personally owned by or registered to a worker. The worker terminal 20 is connected to a network 30 by means of cable or wireless (Wi-Fi (registered trademark)).

The worker terminal 20 analyzes the vital data of the worker P and determines the health state of the worker P on the basis of the analysis results. Additionally, if it is determined that the health state of the worker P is not within the normal range, then the worker terminal 20 notifies the industrial machine control device 50, via the network 30, of the worker's name (or worker ID), the vital data, the health state (outside the normal range), and that no questions (explained below) relating to the health state and/or a safety checklist are to be asked. Additionally, if it is determined that the health state of the worker P is within the normal range, then the worker terminal 20 determines whether or not to ask the worker P questions relating to the health state and/or the safety checklist in accordance with prescribed conditions (when a setting for asking questions has been selected, when the vital data is near the boundary between normal and problematic, when the vital data has largely varied from past vital data (history), when the vital data has deviated by at least a prescribed value from the vital data when healthy, or the like). If it is determined that questions relating to the health state and/or the safety checklist are to be asked, then the worker terminal 20 notifies the industrial machine control device 50, via the network 30, of the worker's name (or worker ID), the vital data, the health state (within the normal range), and that questions relating to the health state and/or the safety checklist are to be asked. Additionally, if it is determined that there is no need to ask the worker P questions relating to the health state and/or the safety checklist, then the worker terminal 20 notifies the industrial machine control device 50, via the network 30, of the worker's name (or worker ID), the vital data, the health state (within the normal range), and that no questions relating to the health state and/or the safety checklist are to be asked.

Thus, the worker terminal 20 determines that the health state of the worker P is normal when the vital data of the worker P is within the prescribed range and determines that the health state of the worker P is abnormal when the vital data of the worker P is outside the prescribed range. Additionally, as a result of the determination, the worker terminal 20 notifies the industrial machine control device 50 of the health state (within or outside the normal range).

The network 30 comprises, for example, a LAN (local area network). The industrial machine operating panel 40 is an operating panel for controlling the supply of electric power to the industrial machine, the actions of the industrial machine, and the like. The industrial machine operating panel 40 is provided with an industrial machine control device 50. The industrial machine control device 50 is connected to the network 30 by cable or wireless (Wi-Fi (registered trademark)).

Upon receiving, from the worker terminal 20, the worker's name (or worker ID), the vital data, the health state (within or outside the normal range), and whether or not questions relating to the health state and/or the safety checklist are to be asked, the industrial machine control device (startup control device) 50 stores the vital data, the health state (within or outside the normal range), and whether or not questions relating to the health state and/or the safety checklist are to be asked, in association with the worker's name (or worker ID). When the worker P selects (inputs) the worker's own name (or worker ID) at the industrial machine operating panel 40 in order to operate the industrial machine 60, the industrial machine control device 50 graphically displays the health state on the basis of the vital data and the health state (within or outside the normal range) received and stored earlier in association with that worker's name (or worker ID).

Additionally, when the health state corresponding to that worker's name (or worker ID) is not within the normal range, the industrial machine control device 50 does not allow startup of the industrial machine 60. Additionally, if the health state is within the normal range and no questions relating to the health state and/or the safety checklist are to be asked, then the industrial machine control device 50 allows startup of the industrial machine 60. Additionally, if the health state corresponding to that worker's name (or worker ID) is within the normal range and questions relating to the health state and/or the safety checklist are to be asked, then the industrial machine control device 50 asks questions relating to the health state and/or the safety checklist in accordance with the worker P, analyzes the replies from the worker P, and determines the health state of the worker P and/or the safety of the work environment on the basis of the analysis results. If it is determined that there is a problem in the health state of the worker P and/or the safety of the work environment, then the industrial machine control device 50 does not allow startup of the industrial machine 60, and if it is determined that there are no problems in the health state of the worker P and/or the safety of the work environment, then the industrial machine control device 50 allows startup of the industrial machine 60.

Thus, the industrial machine control device 50 controls whether or not to allow startup of the industrial machine 60 on the basis of the health state (within or outside the normal range), in other words, the analysis results from the worker terminal 20.

Figure 2:
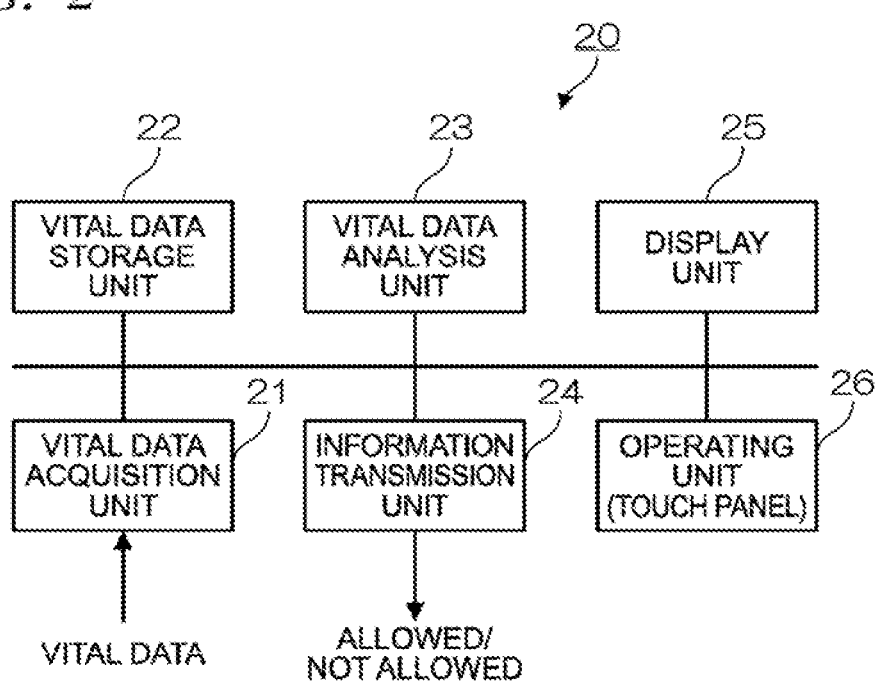
FIG. 2 is a functional block diagram illustrating the functional structure of a worker terminal 20 according to the present first embodiment.

FIG. 2 is a functional block diagram illustrating the functional structure of the worker terminal 20 according to the present first embodiment. The worker terminal 20 is composed of a vital data acquisition unit 21, a vital data storage unit 22, a vital data analysis unit 23, an information transmission unit 24, a display unit 25, and an operating unit (touch panel) 26. These component units are each implemented by means of hardware and/or software (programs).

The vital data acquisition unit 21 acquires vital data measured by the vital data measurement device 10. The vital data storage unit 22 stores vital data acquired by the vital data acquisition unit 21.

The vital data acquisition unit 23 analyzes the vital data stored in the vital data storage unit 22 and determines the health state of the worker P on the basis of the analysis results. The method for determining the health state will be explained. For example, in terms of blood pressure, in general, a diastolic blood pressure of 80 (mmHg) or lower and a systolic blood pressure (contraction-phase blood pressure) of 120 (mmHg) or lower are considered optimal blood pressures, a diastolic blood pressure of 80 to 85 (mmHg) and a systolic blood pressure (contraction-phase blood pressure) of 120 to 130 (mmHg) are considered normal blood pressures, and a diastolic blood pressure of 85 to 90 (mmHg) and a systolic blood pressure (contraction-phase blood pressure) of 130 to 140 (mmHg) are considered normally high blood pressures. Additionally, a diastolic blood pressure of 90 to 100 (mmHg) and a systolic blood pressure (contraction-phase blood pressure) of 140 to 160 (mmHg) are considered to indicate stage I hypertension, a diastolic blood pressure of 100 to 110 (mmHg) and a systolic blood pressure (contraction-phase blood pressure) of 160 to 180 (mmHg) are considered to indicate stage II hypertension, and a diastolic blood pressure of 110 (mmHg) or higher and a systolic blood pressure (contraction-phase blood pressure) of 180 (mmHg) or higher are considered to indicate stage III hypertension.

In the present first embodiment, optimal blood pressures, normal blood pressures, and normally high blood pressures are determined as being normal, and stage I hypertension, stage II hypertension, and stage III hypertension are determined as being abnormal. Additionally, it is also determined as being abnormal when a blood pressure in the normal range changes to enter the hypertension range. Additionally, it is also determined as being abnormal when the blood pressure of a worker P normally in the hypertension range changes from stage I hypertension to stage II hypertension, or changes from stage II hypertension to stage III hypertension or from stage I hypertension to stage III hypertension.

Additionally, for example, in terms of the pulse, a value of 60 to 100 is determined as being normal, and a value lower than 60 (bradycardia) or a value higher than 100 (tachycardia) is determined as being abnormal. Additionally, for example, in terms of body temperature, a value from 35.5 to 37.5° C. is determined as being normal, a value of 39° C. or higher (high fever) is determined as being abnormal, and when the value is 37 to 37.9° C. (slight fever) and 38 to 38.9° C. (medium-level fever), the determination is made in accordance with the type of work (industrial machine 60) or it is compulsorily determined that there is an abnormality.

Additionally, if it is determined that the health state of the worker P is within the normal range, then the vital data analysis unit 23 determines whether or not the worker P is to be further asked questions relating to the health state and/or the safety checklist by means of the industrial machine control device 50. When prescribed conditions (when a setting for asking questions has been selected, when the vital data is near the boundary between normal and problematic, when the vital data has largely varied from past vital data (history), when the vital data has deviated by at least a prescribed value from the vital data when healthy, or the like) are met, the vital data analysis unit 23 determines that further questions relating to the health state and/or the safety checklist should be asked.

If the vital data analysis unit 23 determines that the health state of the worker P is not within the normal range, then the information transmission unit 24 notifies the industrial machine control device 50, via the network 30, of the worker's name (or worker ID), the vital data, the health state (outside the normal range), and that no questions relating to the health state and/or the safety checklist are to be asked. Additionally, if the vital data analysis unit 23 determines that the health state of the worker P is within the normal range and further questions relating to the health state of the worker P and/or the safety checklist are to be asked by the industrial machine control device 50, then the information transmission unit 24 notifies the industrial machine control device 50, via the network 30, of the worker P's name (or worker ID), the vital data, the health state (within the normal range), and that questions relating to the health state and/or the safety checklist are to be asked. Meanwhile, if the vital data analysis unit 23 determines that there is no need to ask any further questions relating to the health state of the worker P and/or the safety checklist, then the information transmission unit 24 notifies the industrial machine control device 50, via the network 30, of the worker P's name (or worker ID), the vital data, the health state (within the normal range), and that no questions relating to the health state and/or the safety checklist are to be asked.

The display unit 25 comprises a liquid crystal display, an organic EL (electroluminescence) display, or the like, and displays various types of input screens, acquired vital data, histories of the vital data, and the like. The operating unit (touch panel) 26 detects direct contact or the proximity of a finger, a stylus (pen), or the like. The operating unit 26 may include a pointing device and mechanical switches and the like, such as a power button and volume buttons.

Figure 3:
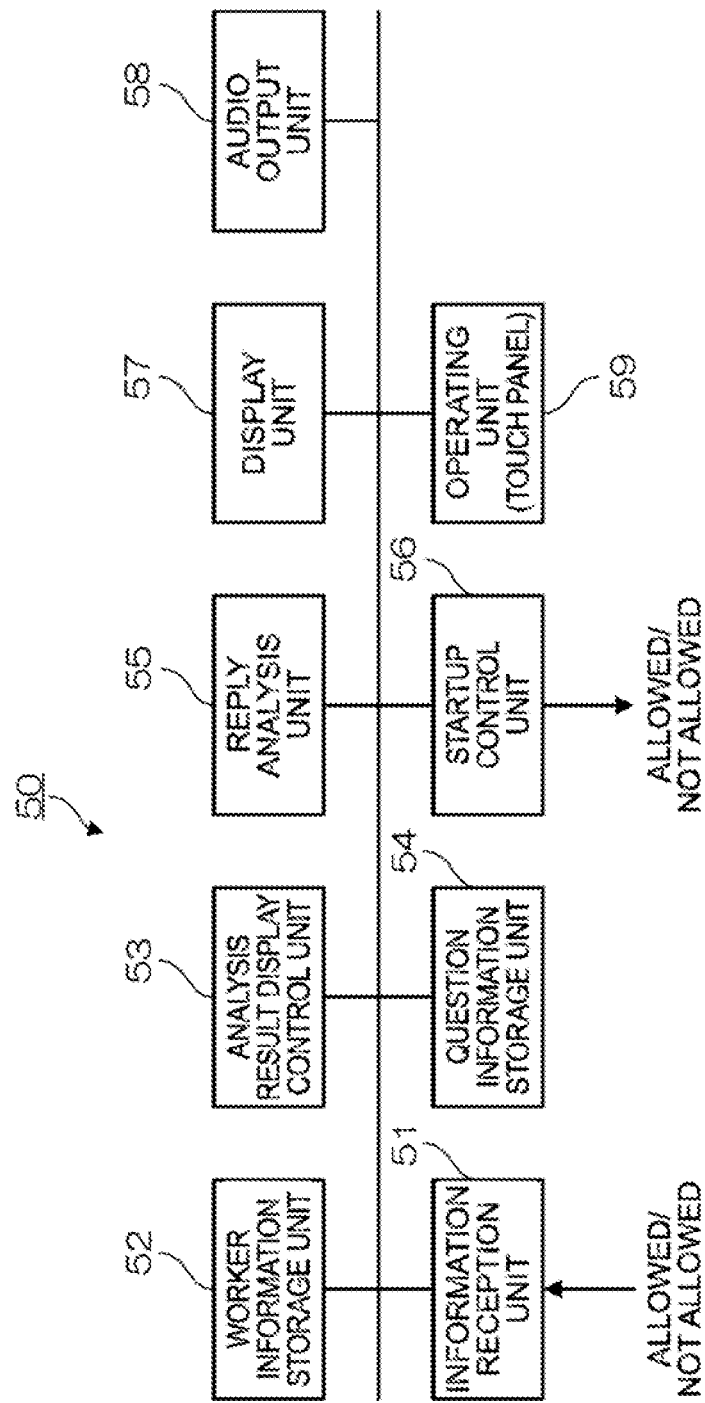
FIG. 3 is a functional block diagram illustrating the functional structure of an industrial machine control device 50 according to the present first embodiment.

FIG. 3 is a functional block diagram illustrating the functional structure of the industrial machine control device 50 according to the present first embodiment. The industrial machine control device 50 is composed of an information reception unit 51, a worker information storage unit 52, an analysis result display control unit 53, a question information storage unit 54, a reply analysis unit 55, a startup control unit 56, a display unit 57, an audio output unit 58, and an operating unit (touch panel) 59. These component units are each implemented by means of hardware and/or software (programs).

The information reception unit 51 receives from the worker terminal 20, via the network 30, the worker's name (or worker ID), the vital data, the health state (within or outside the normal range), and whether or not questions relating to the health state and/or the safety checklist are to be asked. The worker information storage unit 52 stores the worker P's name (or worker ID), the vital data, the health state (within or outside the normal range), and whether or not questions relating to the health state and/or the safety checklist are to be asked.

The analysis result display control unit 53 references the worker information storage unit 52, and on the basis of the vital data and health state (within or outside the normal range) corresponding to the worker P's name (or worker ID), displays the health state of the worker as a graphical screen on the display unit 57. The question information storage unit 54 stores question information relating to the health state of the worker P and a startup safety checklist. The question information may be classified in accordance with the department to which the worker P belongs, the worker P's skill level, the type of work, and the like.

If further questions relating to the health state of the worker P and/or the safety checklist are to be asked, then the reply analysis unit 55 references the question information storage unit 54, displays question information for asking questions relating to the health state of the worker P and/or the safety checklist on the display unit 57, analyzes the worker P's replies to the questions, and on the basis of the analysis results, determines whether or not there is a problem in the health state of the worker P and/or the safety of the work environment.

If the health state of the worker P is outside the normal range, then the startup control unit 56 executes a process for not allowing startup of the industrial machine 60. Additionally, if the health state of the worker P is within the normal range and no questions relating to the health state and/or the safety checklist are to be asked, then the startup control unit 56 executes a process for allowing startup of the industrial machine 60. Meanwhile, if the health state of the worker P is within the normal range and questions relating to the health state and/or the safety checklist are to be asked, then the startup control unit 56 executes a process for allowing startup of the industrial machine 60 if it is determined, by the reply analysis unit 55, that there are no problems in the health state of the worker P and/or the safety of the work environment. Additionally, if the health state of the worker P is within the normal range and questions relating to the health state and/or the safety checklist are to be asked, then the startup control unit 56 executes a process for not allowing startup of the industrial machine 60 if it is determined, by the reply analysis unit 55, that there is a problem in the health state of the worker P and/or the safety of the work environment.

The display unit 57 comprises a liquid crystal display, an organic EL (electroluminescence) display, or the like, and displays the health state (within or outside the normal range), the vital data, questions relating to the health state, questions relating to the startup safety checklist, and the like. The audio output unit 58 plays and outputs, as audio, the questions relating to the health state and/or the safety checklist. The operating unit (touch panel) 59 detects direct contact or the proximity of a finger, a stylus (pen), or the like. The operating unit (touch panel) 59 may include a pointing device and mechanical switches and the like, such as a power button and volume buttons.

Figure 4:
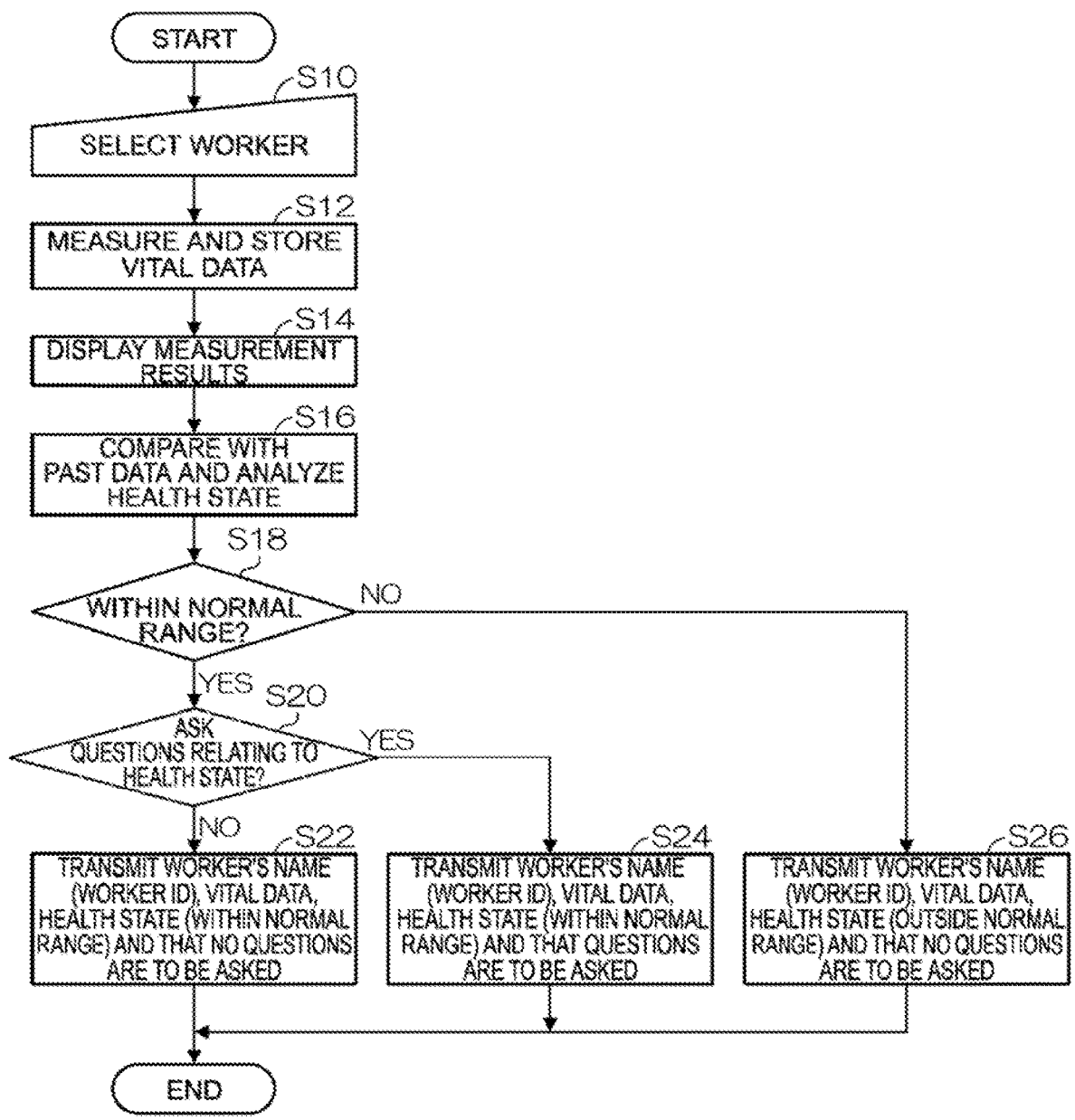
FIG. 4 is a flow chart for explaining the actions of the worker terminal 20 according to the present first embodiment.

FIG. 4 is a flow chart for explaining the actions of the worker terminal 20 according to the first embodiment of the present invention. Additionally, FIGS. 6 to 13 are schematic diagrams illustrating display screens on the worker terminal 20 according to the present first embodiment.

First, before commencing work using the industrial machine 60, the worker P starts an application for measuring vital data by means of the worker terminal 20, and also establishes a link between the vital data measurement device 10 and the worker terminal 20 by means of a prescribed communication format (for example, Bluetooth (registered trademark)).

Figure 6:
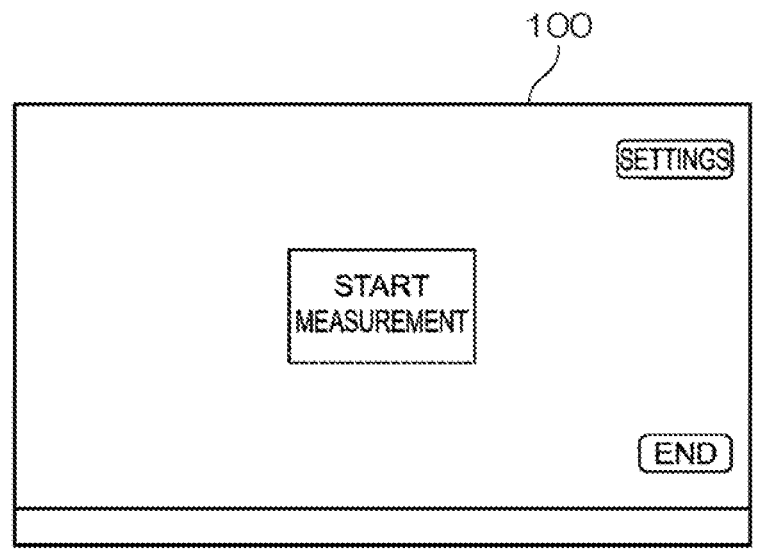
FIG. 6 is a schematic view illustrating a display screen on the worker terminal 20 according to the present first embodiment.

The worker terminal 20 first prompts the worker P to select a measurer (i.e., the worker P) who is to measure the vital data (step S10). More specifically, an application in the worker terminal 20, as illustrated in FIG. 6, displays a screen 100 for starting the measurement of the vital data. The screen 100 displays a "Start measurement" button for providing an instruction to start measuring the vital data, a "Settings" button for setting parameters relating to the measurement of the vital data, and an "End" button for ending the application.

Figure 7:
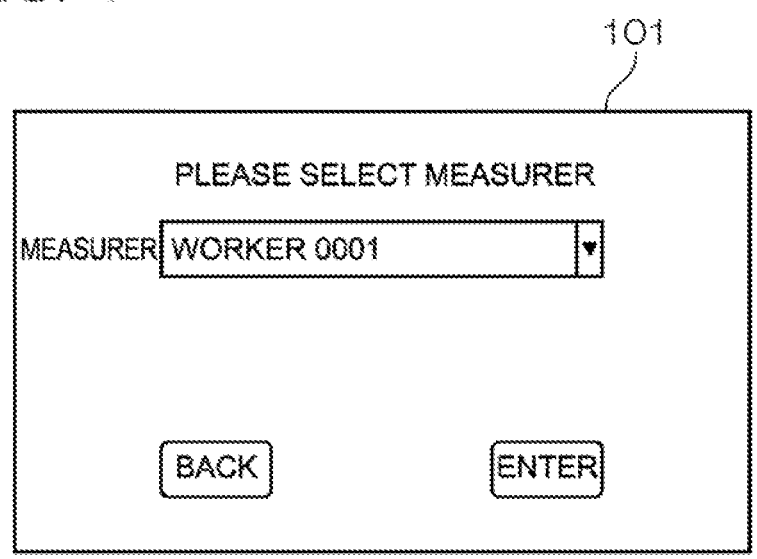
FIG. 7 is a schematic view illustrating a display screen on the worker terminal 20 according to the present first embodiment.

Next, when the worker P selects (touches) the "Start measurement" button, the worker terminal 20 displays a screen 101 for selecting the name of the worker (measurer), as illustrated in FIG. 7. The screen 101 displays a pull-down menu for selecting the name of the worker (measurer), a "Back" button for returning to the previous screen, and an "Enter" button for choosing the name of the worker (measurer) that has been selected. The worker P selects the worker (measurer) from the pull-down menu on screen 101, and selects (touches) the "Enter" button.

Figure 8:
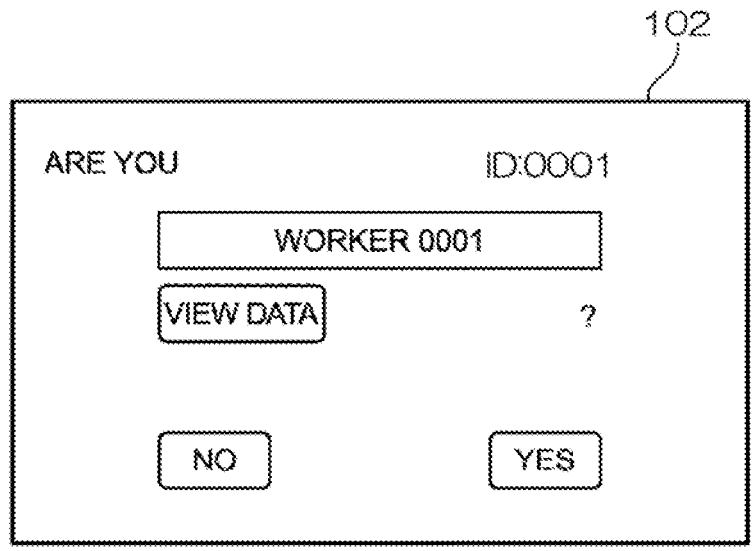
FIG. 8 is a schematic view illustrating a display screen on the worker terminal 20 according to the present first embodiment.

When the "Enter" button is selected (touched) by the worker P, the worker terminal 20 displays the screen 102 illustrated in FIG. 8, for confirming that the name of the selected worker (measurer) is not mistaken. The screen 102 displays the ID of the selected worker (measurer), the name of the selected worker (measurer), a "View data" button for viewing information (such as vital data histories) relating to the displayed worker (measurer), a "No" button for indicating that the display is incorrect, and a "Yes" button for indicating that the display is correct. The worker P checks the name of the worker (measurer) that is displayed on the screen 102 and selects (touches) the "Yes" button.

Figure 9:
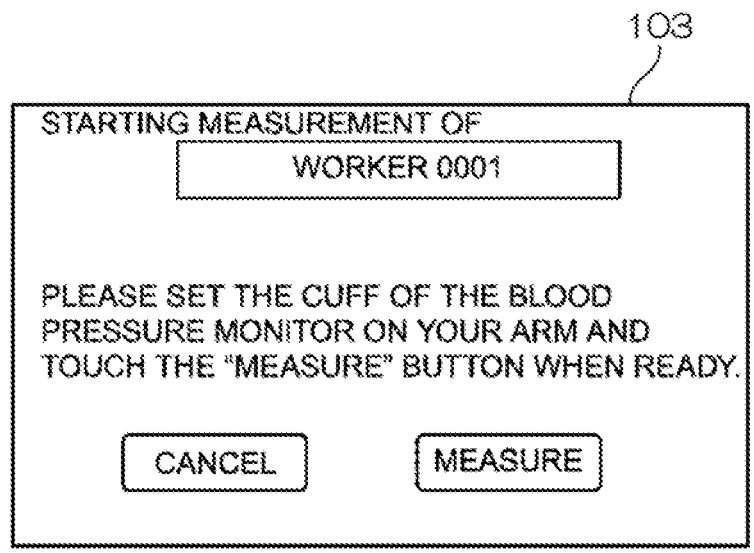
FIG. 9 is a schematic view illustrating a display screen on the worker terminal 20 according to the present first embodiment.

When the "Yes" button on the screen 102 is selected (touched) by the worker P, the worker terminal 20 starts measuring the vital data by means of the vital data measurement device 10, and collects and stores the measured vital data (step S12; collection function). More specifically, the application in the worker terminal 20 first displays, on the display unit 25, a screen 103 for notifying the worker P that the measurement of the vital data is to be started, as illustrated in FIG. 9. The screen 103 displays the name of the worker (measurer), a message notifying the worker that the measurement is to start, a message prompting the worker to prepare to start the measurement, a "Cancel" button for stopping the measurement of the vital data, and a "Measure" button for starting the measurement of the vital data.

The worker P, following the message on the screen 103, attaches the vital data measurement device 10. In this case, as an example, the vital data measurement device 10 is assumed to be a blood pressure monitor for measuring blood pressure (including the pulse) and a clinical thermometer for measuring body temperature. Additionally, the clinical thermometer may, aside from a common clinical thermometer, be a radiation thermometer or the like. When ready, the worker P selects (touches) the "Measure" button on the screen 103.

Figure 10:
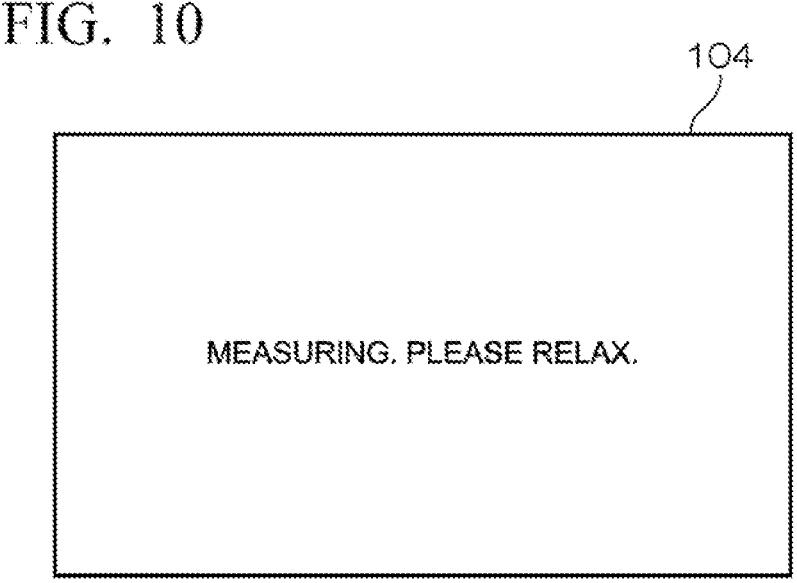
FIG. 10 is a schematic view illustrating a display screen on the worker terminal 20 according to the present first embodiment.

When the "Measure" button on the screen 103 is selected (touched) by the worker P, the worker terminal 20 starts measuring the vital data by means of the vital data measurement device 10. The vital data acquisition unit 21 collects vital data by means of the vital data measurement device 10. While the vital data is being measured by the vital data measurement device 10, the worker terminal 20 displays, on the display unit 25, a screen 104 for notifying the worker P that the measurement is in progress, as illustrated in FIG. 10. The screen 104 displays a message notifying the worker P that the measurement is in progress.

Figure 11:
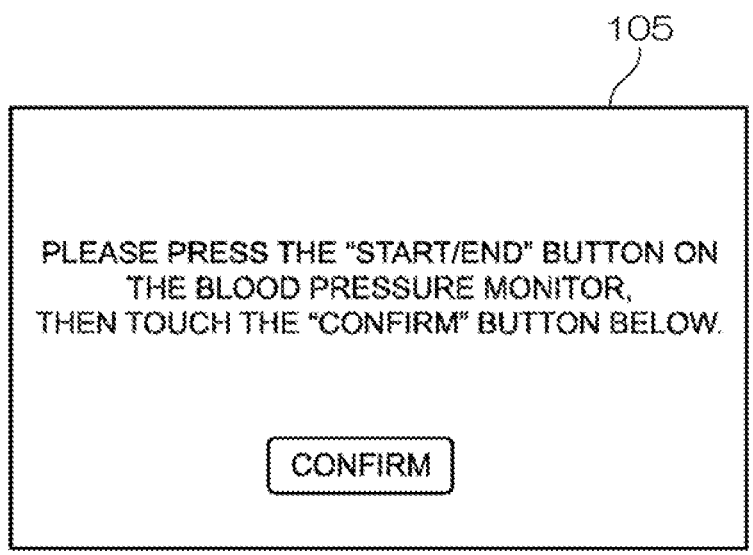
FIG. 11 is a schematic view illustrating a display screen on the worker terminal 20 according to the present first embodiment.

Next, as shown in FIG. 11, the worker terminal 20 displays, on the display unit 25, a screen 105 for confirming that the measurement of the vital data has ended, as illustrated in FIG. 11. The screen 105 displays a message for instructing the worker P to perform an operation to end the measurement by the vital data measurement device 10, and a "Confirm" button for confirming that the ending operation has been performed.

The worker P views the message on the screen 105, performs the operation for ending the measurement by the vital data measurement device 10, and selects (touches) the "Confirm" button on the screen 105. While the vital data is being measured, the screen 104 illustrated in FIG. 10 and the screen 105 illustrated in FIG. 11 may be displayed so as to alternate at a prescribed time interval. After performing the operation for ending the measurement of the vital data by the vital data measurement device 10, the worker P merely needs to select (touch) the "Confirm" button at a time during which the screen 105 illustrated in FIG. 11 is displayed.

Figures 12, 13:
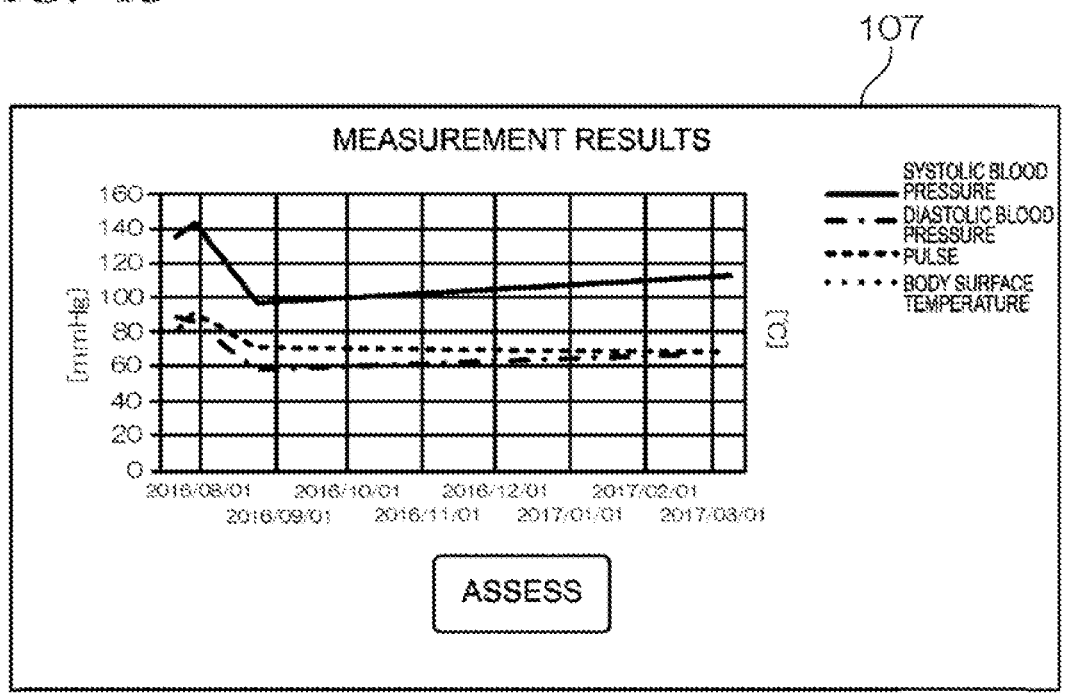
FIG. 12 is a schematic view illustrating a display screen on the worker terminal 20 according to the present first embodiment.
FIG. 13 is a schematic view illustrating a display screen on the worker terminal 20 according to the present first embodiment.

When the "Confirm" button on the screen 105 is selected (touched) by the worker P, the worker terminal 20 displays, on the display unit 25, a screen 106 for confirming the measured vital data, as illustrated in FIG. 12 (step S14). The screen 106 displays the name of the worker P, the measured vital data (in the illustrated example, the systolic blood pressure, the diastolic blood pressure, the pulse, and the body temperature), a message asking whether or not the measured vital data is to be registered, a "Cancel" button for cancelling the registration of the measured vital data, and a "Register" button for registering the measured vital data. The worker P views the vital data on the screen 106, and if satisfied therewith, selects (touches) the "Register" button on the screen 106.

When the "Register" button on the screen 106 is selected (touched) by the worker P, the worker terminal 20 stores the vital data of the worker P measured by the vital data measurement device 10 in the vital data storage unit 22.

Additionally, the worker terminal 20 displays, on the display unit 25, a screen 107 on which the history (change in the vital data during a prescribed period of time) of the vital data of the worker P is graphed, as illustrated in FIG. 13. The screen 107 displays a graph of the history (in the illustrated example, approximately eight months' worth) of the vital data of the worker P, and an "Assess" button for instructing that the health state of the worker P should be assessed.

The vital data analysis unit 23 of the worker terminal 20, for example, compares the measured vital data with past vital data to analyze the health state of the worker P (step S16; health state determination function). On the basis of the health state analysis results, the vital data analysis unit 23 determines whether or not the health state of the worker P is within the normal range (or the vital data is within the normal range) (step S18; health state determination function). Furthermore, if it is determined that the health state of the worker P is not within the normal range (or the vital data is not within the normal range) (NO in step S18), then the information transmission unit 24 determines that the health state is abnormal, and notifies the industrial machine control device 50, via the network 30, of the worker's name (or worker ID), the vital data, the health state (outside the normal range), and that no questions relating to the health state and/or the safety checklist are to be asked (step S26). Thereafter, the process ends.

Meanwhile, if it is determined that the health state of the worker P is within the normal range (or the vital data is within the normal range) (YES in step S18), then the vital data analysis unit 23 determines that the health state is normal, and determines whether or not to further ask the worker P questions relating to the health state and/or the safety checklist by means of the industrial machine control unit 50 in accordance with prescribed conditions (when a setting for asking questions has been selected, when the vital data is near the boundary between normal and problematic, when the vital data has largely varied from past vital data (history), when the vital data has deviated by at least a prescribed value from the vital data when healthy, or the like) (step S20). Furthermore, if it is determined that the worker P needs to be asked further questions relating to the health state and/or the safety checklist (YES in step S20), then the information transmission unit 24 notifies the industrial machine control device 50, via the network 30, of the worker P's name (or worker ID), the vital data, the health state (within the normal range), and that questions relating to the health state and/or the safety checklist are to be asked (step S24). Thereafter, the process ends.

Meanwhile, if the vital data analysis unit 23 determines that the health state of the worker P is within the normal range (or the vital data is within the normal range) (YES in step S18) and there is no need to ask any further questions relating to the health state of the worker P by means of the industrial machine control device 50 (NO in step S20), then the information transmission unit 24 notifies the industrial machine control device 50, via the network 30, of the worker P's name (or worker ID), the vital data, the health state (within the normal range), and that no questions relating to the health state and/or the safety checklist are to be asked (step S22). Thereafter, the process ends.

Thus, by means of the health state determination function, it is determined whether the worker P's health state is normal or abnormal on the basis of the vital data of the worker P before the work.

Figure 5:
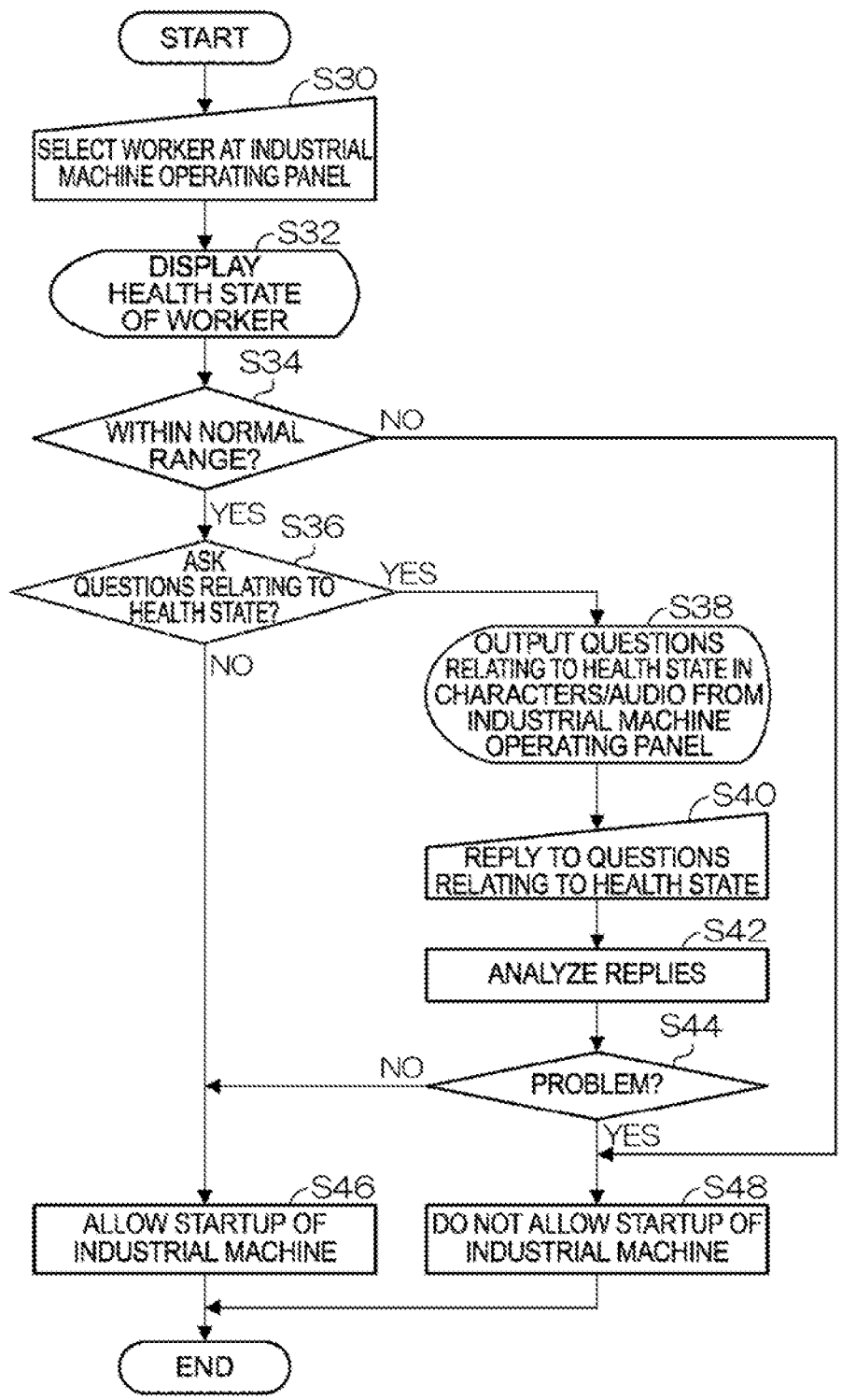
FIG. 5 is a flow chart for explaining the actions of the industrial machine control device 50 according to the present first embodiment.

FIG. 5 is a flow chart for explaining the actions of the industrial machine control device 50 according to the present first embodiment. Additionally, FIGS. 14 to 22 are schematic diagrams illustrating display screens of the industrial machine control device 50 according to the present first embodiment.

When the measurement of the vital data ends, the worker P moves to the location of the industrial machine operating panel 40 in order to operate the industrial machine 60. The industrial machine control device 50 prompts the worker P to select the worker P's name (or worker ID) (step S30). The industrial machine control device 50 references the worker information storage unit 52 in accordance with the name (or worker ID) selected by the worker P, and on the basis of the vital data and the health state (within or outside the normal range) corresponding to the worker ID, received earlier from the worker terminal 20, displays a graphic representing the health state of the worker P on the display unit 57, as illustrated in one of FIGS. 14 to 19 (step S32).

Figure 14:
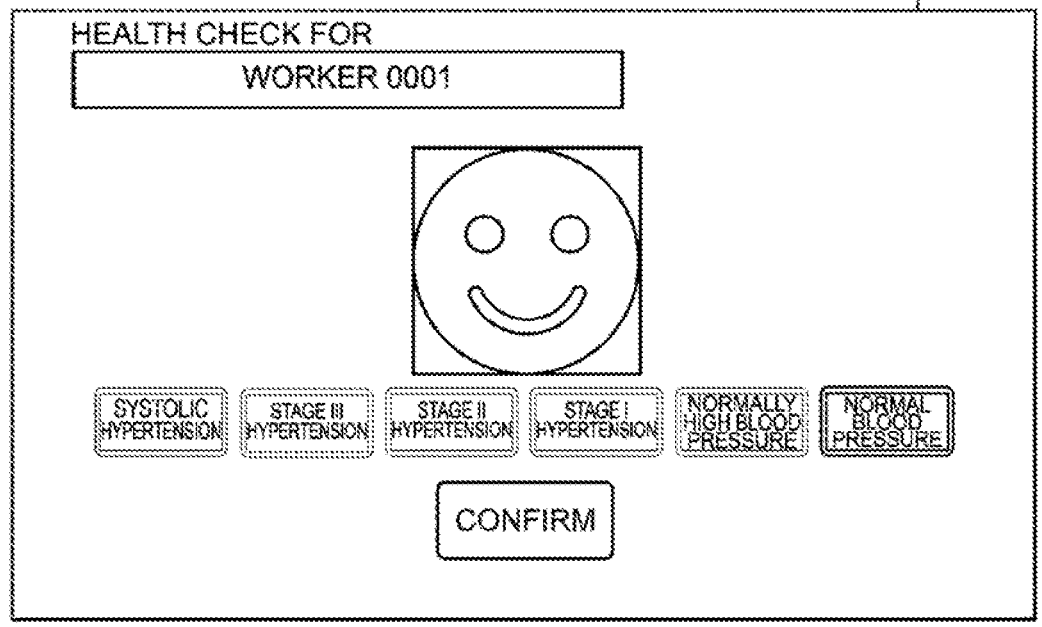
FIG. 14 is a schematic view illustrating a display screen on the industrial machine control device 50 according to the present first embodiment.

For example, when indicating that the health state is within the normal range, the industrial machine control device 50 displays, on the display unit 57, a screen 108 indicating that the health state is within the normal range, as illustrated in FIG. 14. The screen 108 displays the name of the worker P, a smiling-face graphic indicating that the health state is within the normal range, icons highlighting that the vital data indicates a blood pressure within the normal blood pressure range (in the illustrated example, the "Normal blood pressure" icon is highlighted), and a "Confirm" button for indicating that the analysis results have been viewed.

Figure 15:
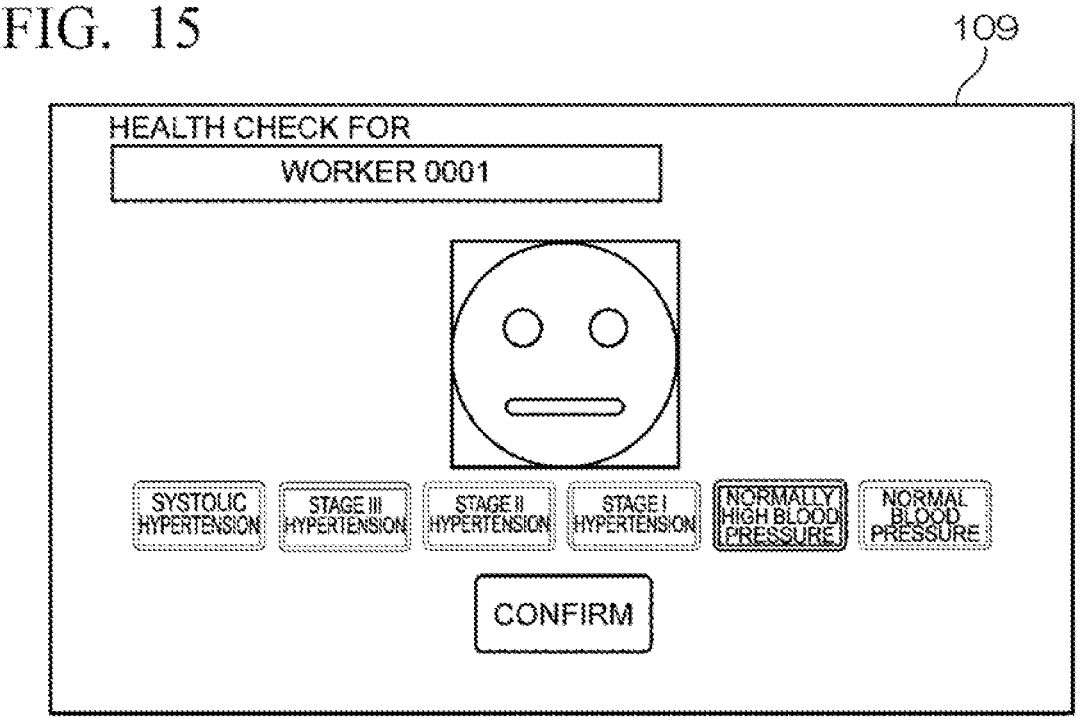
FIG. 15 is a schematic view illustrating a display screen on the industrial machine control device 50 according to the present first embodiment.

Additionally, for example, when indicating that the health state of the worker P is within the normal range but that there is a slight tendency towards high blood pressure (normally high blood pressure), the industrial machine control device 50 displays, on the display unit 57, a screen 109 indicating that the health state is within the normal range, as illustrated in FIG. 15. The screen 109 displays the name of the worker P, a neutral-face graphic indicating that the vital data includes a blood pressure outside the normal blood pressure range but that the health state is within the normal range, icons highlighting that the vital data indicates a blood pressure within the normally high blood pressure range (in the illustrated example, the "Normally high blood pressure" icon is highlighted), and a "Confirm" button for indicating that the analysis results have been viewed.

Figure 16:
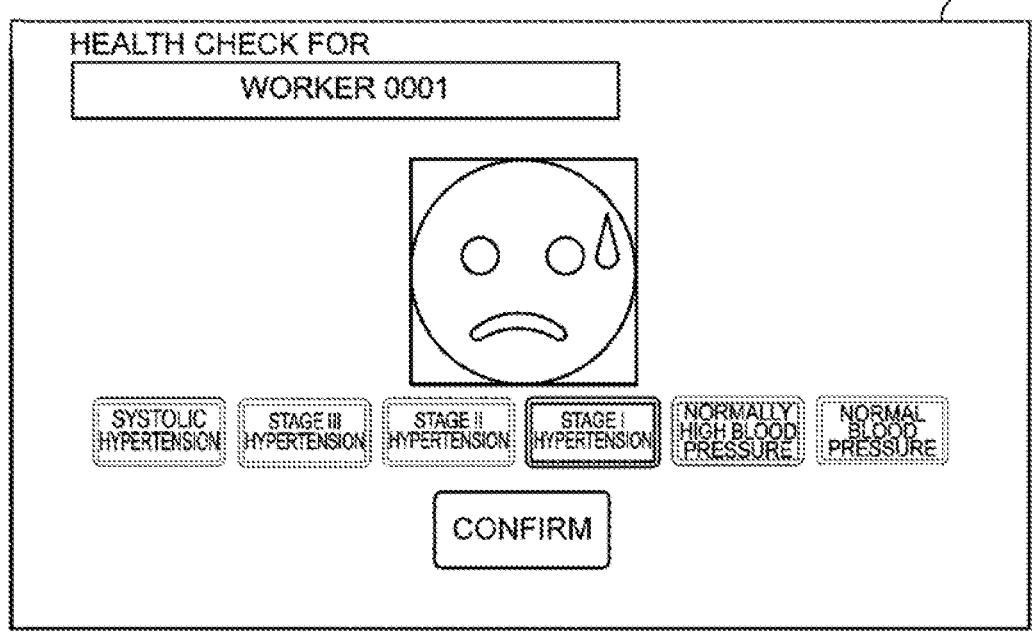
FIG. 16 is a schematic view illustrating a display screen on the industrial machine control device 50 according to the present first embodiment.

Additionally, for example, when indicating that the health state of the worker P is not within the normal range, the industrial machine control device 50 displays, on the display unit 57, a screen 110 indicating that the health state is not within the normal range, as illustrated in FIG. 16. The screen 110 displays the name of the worker P, a frowning-face graphic indicating that the health state is not within the normal range (that caution is necessary), icons highlighting that the vital data includes a blood pressure within the stage I hypertension range (in the illustrated example, the "Stage I hypertension" icon is highlighted), and a "Confirm" button for indicating that the analysis results have been viewed.

Figure 17:
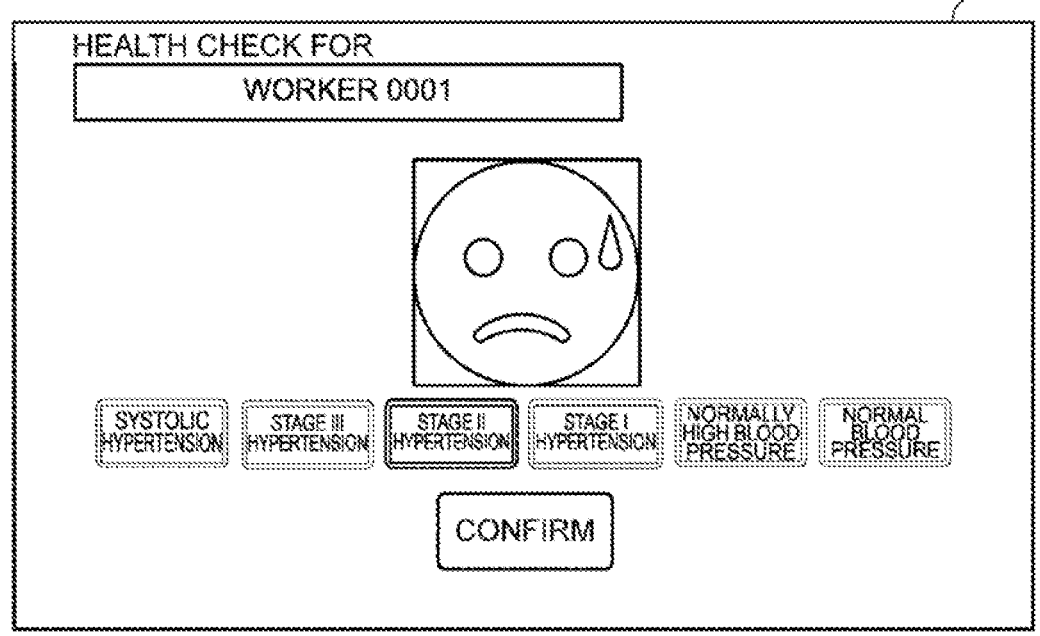
FIG. 17 is a schematic view illustrating a display screen on the industrial machine control device 50 according to the present first embodiment.

Additionally, for example, when indicating that the health state of the worker P is not within the normal range, the industrial machine control device 50 displays, on the display unit 57, a screen 111 indicating that the health state is not within the normal range, as illustrated in FIG. 17. The screen 111 displays the name of the worker P, a frowning-face graphic indicating that the health state is not within the normal range (that caution is necessary), icons highlighting that the vital data includes a blood pressure within the stage II hypertension range (in the illustrated example, the "Stage II hypertension" icon is highlighted), and a "Confirm" button for indicating that the analysis results have been viewed.

Figure 18:
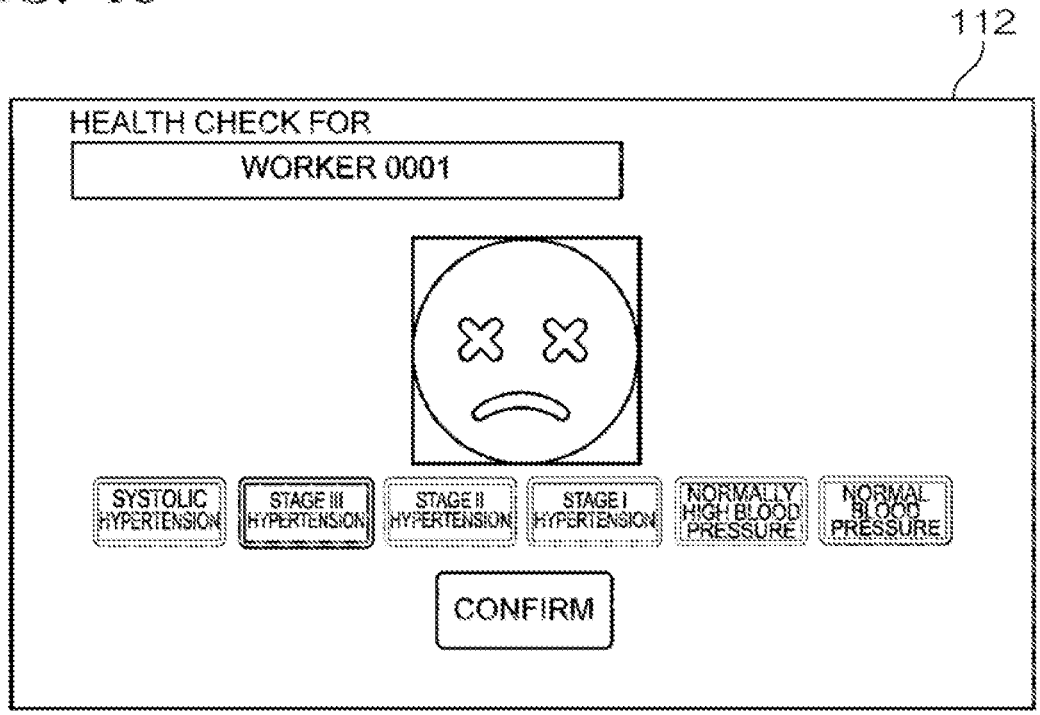
FIG. 18 is a schematic view illustrating a display screen on the industrial machine control device 50 according to the present first embodiment.

Additionally, for example, when indicating that the health state of the worker P is not within the normal range, the industrial machine control device 50 displays, on the display unit 57, a screen 112 indicating that the health state is abnormal, as illustrated in FIG. 18. The screen 112 displays the name of the worker P, a dazed-face graphic indicating that the health state is abnormal, icons highlighting that the vital data includes a blood pressure within the stage III hypertension range (in the illustrated example, the "Stage III hypertension" icon is highlighted), and a "Confirm" button for indicating that the analysis results have been viewed.

Figure 19:
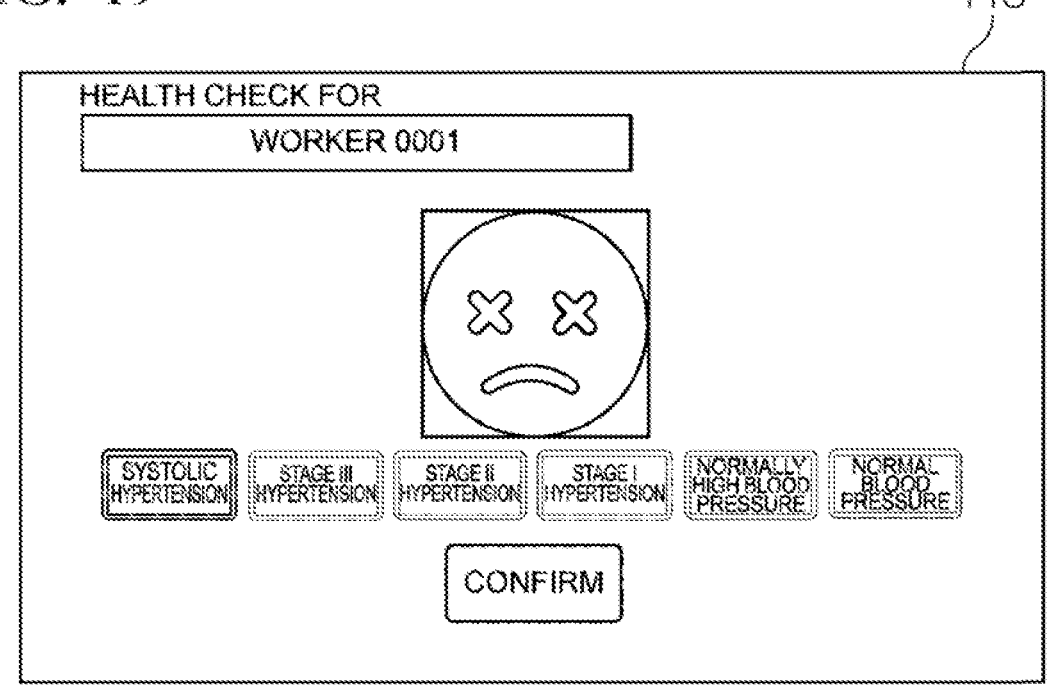
FIG. 19 is a schematic view illustrating a display screen on the industrial machine control device 50 according to the present first embodiment.

Additionally, for example, when indicating that the health state of the worker P is not within the normal range, the industrial machine control device 50 displays, on the display unit 57, a screen 113 indicating that the health state is abnormal, as illustrated in FIG. 19. The screen 113 displays the name of the worker P, a dazed-face graphic indicating that the health state is abnormal, icons highlighting that the vital data includes a blood pressure within the systolic hypertension range (in the illustrated example, the "Systolic hypertension" icon is highlighted), and a "Confirm" button for indicating that the analysis results have been viewed.

Next, when the "Confirm" button on the screen 108 to the screen 113 is selected (touched) by the worker P, the industrial machine control device 50 references the worker information storage unit 52. And the industrial machine control device 50 determines, from the health state (within or outside the normal range) determined on the basis of the vital data of the worker P before the work using the industrial machine 60, corresponding to the worker ID, received earlier from the worker terminal 20, whether or not the health state of the worker P is within the normal range (or the vital data is within the normal range) (step S34; control function). Furthermore, if it is determined that the health state of the worker P is not within the normal range (or the vital data is not within the normal range) (NO in step S34), then the startup control unit 56 in the industrial machine control device 50 does not allow startup of the industrial machine 60 (step S48; control function). In other words, the startup control unit 56 turns off the startup of the industrial machine 60. Thereafter, the process ends. In this case, the worker P cannot perform work using the industrial machine 60.

Meanwhile, if the health state of the worker P is within the normal range (or the vital data is within the normal range) (YES in step S34), then the industrial machine control device 50 references the worker information storage unit 52 and determines whether or not questions relating to the health state and/or the safety checklist are to be asked (step S36). Furthermore, if the worker P is not to be asked questions relating to the health state and/or the safety checklist (NO in step S36), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if the health state of the worker P is within the normal range (or the vital data is within the normal range) and questions relating to the health state and/or the safety checklist are to be asked (YES in step S36), then the industrial machine control device 50 references the question information storage unit 54. And the industrial machine control device 50 reads out question information relating to the health state and/or the safety checklist (work-related cautions) in accordance with the department to which the worker P belongs, the skill level of the worker P, or the like. And the industrial machine control device 50 displays the question information on the display unit 57 or outputs the question information as audio from the audio output unit 58 (step S38; health state question presentation function, cautionary question presentation function, and output function).

Figures 20, 21:
FIG. 20 is a schematic view illustrating a display screen on the industrial machine control device 50 according to the present first embodiment.
FIG. 21 is a schematic view illustrating a display screen on the industrial machine control device 50 according to the present first embodiment.

FIG. 20 illustrates an example of the questions relating to the health state and/or the safety checklist. As illustrated in FIG. 20, the industrial machine control device 50 displays, on the display unit 57, a screen 114 showing questions, regarding the health state, whether the worker P is feeling well, and regarding the safety checklist, whether there are any people within the equipment, whether protective gear is being worn, whether or not anything has been left within the equipment, and the like, as well as options for selecting replies to the respective questions. Thus, the questions include, in addition to questions relating to the health of the worker P, questions relating to the safety checklist to be checked when starting the work. The industrial machine control device 50 presents work-related cautions to the worker P in question form, determines whether or not there is a problem in the work starting conditions on the basis of the worker P's replies to the questions, and controls whether or not to allow startup of the industrial machine 60 on the basis of the determination result. As a result thereof, it is possible to ensure safety not only in terms of the health of the worker P, but also in terms of the work environment for performing work using the industrial machine 60.

The industrial machine control device 50 inputs the replies provided by the worker P to the questions on the screen 114 (step S40), and the reply analysis unit 55 analyzes the replies to the questions relating to the health state and/or the safety checklist (step S42; health state reply determination function, cautionary reply determination function). Furthermore, in accordance with the results of the analysis of the questions relating to the health state and/or the safety checklist, the reply analysis unit 55 displays, on the display unit 57, a screen 115 indicating the results of the analysis of the replies to the questions relating to the health state and/or the safety checklist, as illustrated in FIG. 21. The screen 115 displays the name of the worker P, a graphic of a face representing the health state, icons in which the health state is highlighted, and a "Confirm" button for indicating that the analysis results have been viewed.

Next, the reply analysis unit 55 in the industrial machine control device 50 determines whether or not there is a problem in the health state of the worker P and/or the safety, based on the results of the analysis of the replies to the questions relating to the health state (step S44; health state reply determination function, cautionary reply determination function). Furthermore, if it is determined that there are no problems in the health state of the worker P and/or the safety (NO in step S44), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if there is a problem in the health state of the worker P and/or the safety (YES in step S44), then the startup control unit 56 does not allow startup of the industrial machine 60 (step S48; control function). In other words, the startup control unit 56 turns off the startup of the industrial machine 60. Thereafter, the process ends. In this case, the worker P cannot perform work using the industrial machine 60.

Additionally, FIG. 22 shows another example of the questions relating to the health state. As illustrated in FIG. 22, the industrial machine control device 50 may display, on the display unit 57, a screen 116 displaying, as a startup safety checklist, questions such as whether the worker P is feeling well, whether protective gear is being worn, whether there are any people within the equipment, whether a door is closed for certain, whether a protective cover has been attached, whether a lid is open, whether protective devices or sensors are malfunctioning, and the like, as well as options for selecting replies to the respective questions. In other words, in addition to the questions relating to the health of the worker P, the startup safety checklist includes questions relating to a safety checklist to be checked when starting work. The industrial machine control device 50 presents work-related cautions to the worker P in question form, determines whether or not there is a problem in the work starting conditions in addition to the health state of the worker P on the basis of the worker P's replies to the inquiries made in question form, and on the basis of the determination result, controls whether or not to allow startup of the industrial machine 60. As a result thereof, it is possible to ensure not only the health of the worker P, but also the safety of the work environment for performing work using the industrial machine 60.

According to the above-mentioned first embodiment, the worker terminal 20 can be used to analyze vital data of the worker P measured by the vital data measurement device 10, to determine the health state of the worker P based on the analysis results, to notify the industrial machine control device 50, via the network 30, of the worker's name (or worker ID), the vital data, the health state (within or outside the health range), and whether or not questions relating to the health state and/or the safety checklist are to be asked. And the industrial machine control device 50 can be used to control whether or not to allow startup of the industrial machine in accordance with the notification from the worker terminal 20, so it is possible to control the startup of the industrial machine in accordance with the health state of the worker. As a result thereof, it is possible to prevent deterioration of the health state of the worker P during operating work, and interruption of the operation during work in connection therewith. Therefore, the industrial machine can easily be operated as planned and damage to the industrial machine due to sudden stoppage of the industrial machine or the like can be prevented.

Additionally, according to the above-mentioned first embodiment, if the vital data analysis unit 23 in the worker terminal 20 determines that there are no problems in the health state of the worker P, but it is determined that there is a need to ask the worker P further questions relating to the health state and/or the safety checklist, then the reply analysis unit 55 in the industrial machine control device 50 presents questions relating to the health state and/or the safety checklist to the worker P and determines whether or not there is a problem relating to the health state of the worker P and/or the safety based on the worker P's replies to the questions. Thus, the health state of the worker P and/or the safety can be more accurately determined, and it becomes possible to ensure safety not only in terms of the health of the worker P, but also in terms of the work environment for performing work using the industrial machine 60.

B. Second Embodiment

Next, a second embodiment of the present invention will be explained.

Figure 23:
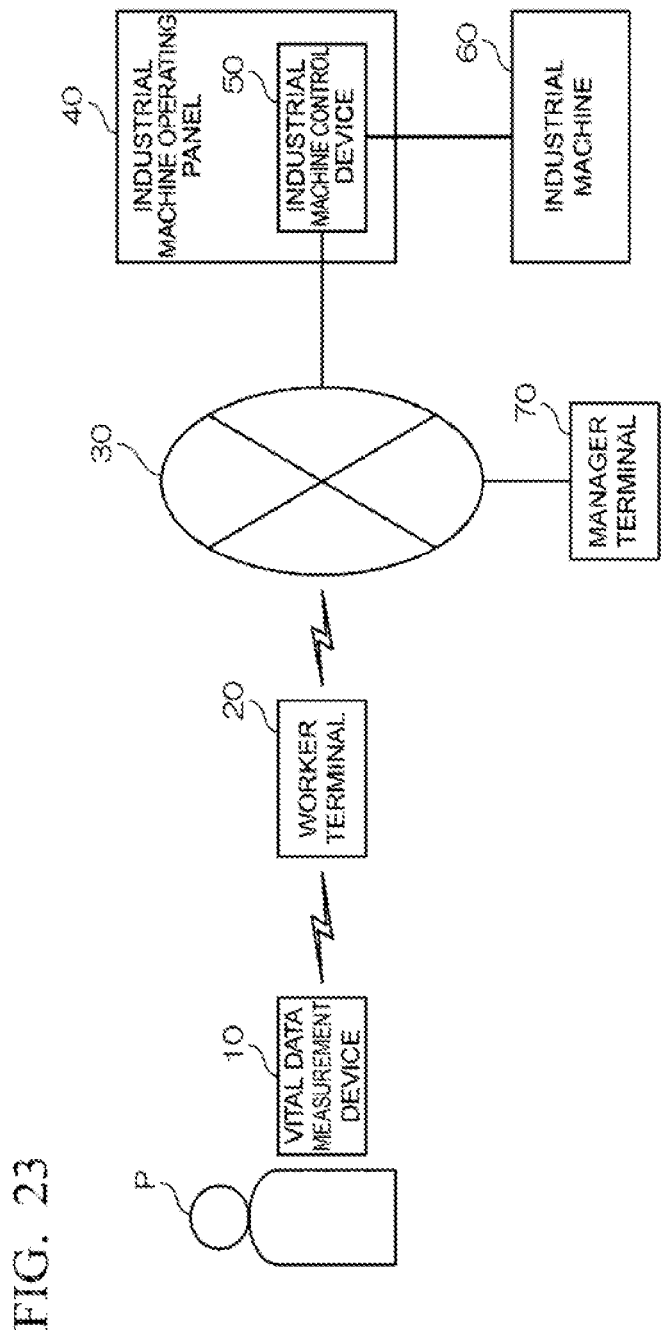
FIG. 23 is a block diagram illustrating the structure of an industrial machine startup control system 1 according to a second embodiment of the present invention.

FIG. 23 is a block diagram illustrating the structure of an industrial machine startup control system 1 according to the second embodiment of the present invention. The portions corresponding to those in FIG. 1 are assigned the same reference symbols and the descriptions thereof will be omitted.

In addition to the above-mentioned features of the first embodiment, the present second embodiment is provided with a manager terminal 70 that is connected, via cable or wireless, to the network 30. The manager terminal 70 is a terminal that is owned by a manager, who is the worker P's superior. In the present second embodiment, if the health state of the worker P is not within the normal range (or the vital data is not within the normal range), or if the health state of the worker P is within the normal range (or the vital data is within the normal range) but it is determined that there is a problem in the health state and/or the safety checklist, then the industrial machine control device 50 alerts the manager terminal 70. When the manager terminal 70 is alerted, the manager determines, from the health state of the worker P and/or the safety, and the vital data, whether or not the worker P can perform the work, whether the worker P should be replaced with another worker, and finally, whether or not the industrial machine should be started. The industrial machine control device 50 is then notified from the manager terminal 70. The industrial machine control device 50 controls whether or not to allow startup of the industrial machine 60 in accordance with the final determination from the manager terminal 70.

Figure 24:
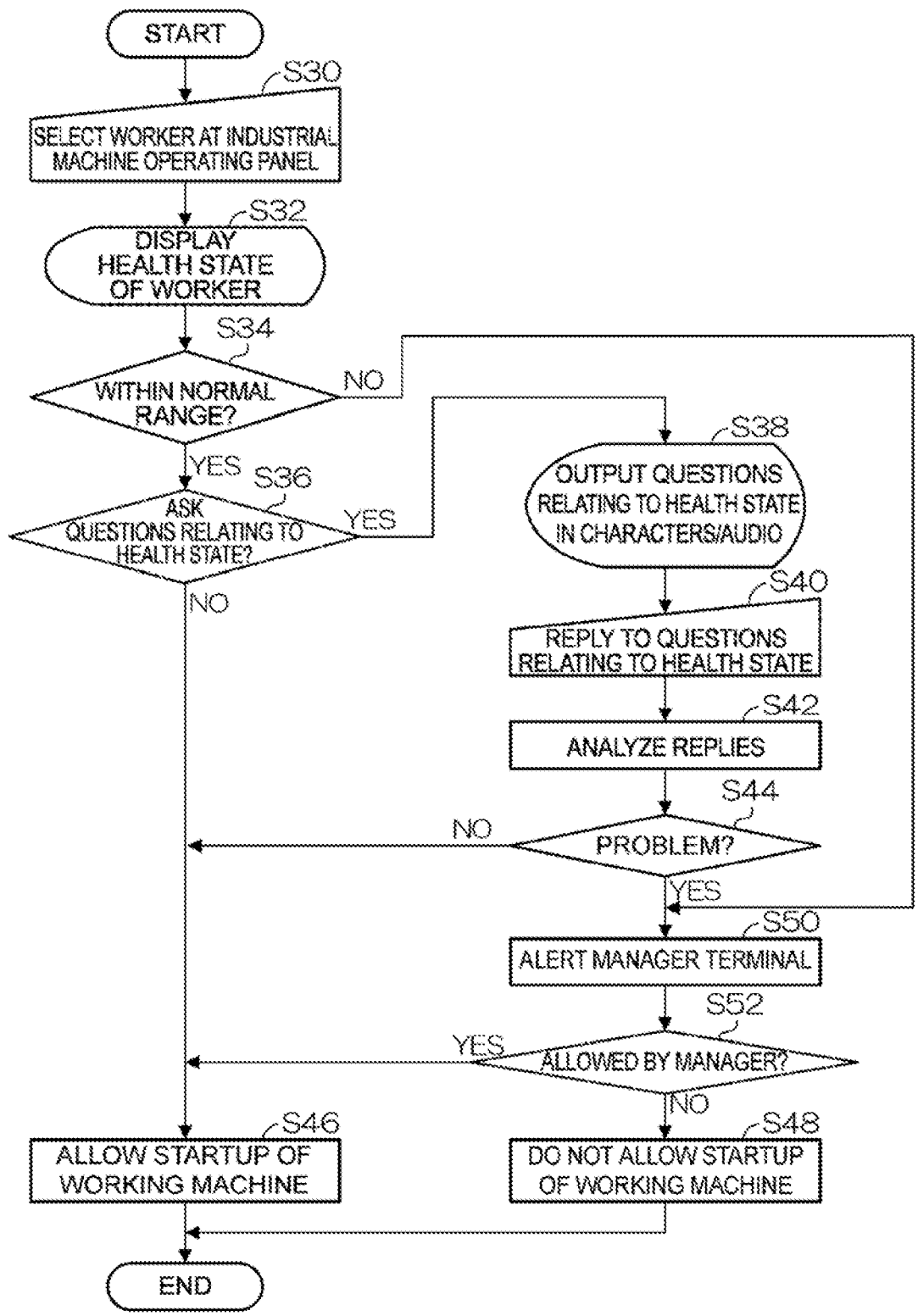
FIG. 24 is a flow chart for explaining the actions of the industrial machine control device 50 according to the present second embodiment.

FIG. 24 is a flow chart for explaining the actions of the industrial machine control device 50 according to the present second embodiment. The steps corresponding to those in FIG. 5 are assigned the same reference symbols and the descriptions thereof will be simplified. Additionally, the actions of the worker terminal 20 according to the present second embodiment are the same as those in the above-mentioned first embodiment, so they will be described with reference to FIG. 4.

First, the worker P starts an application for measuring vital data by means of the worker terminal 20, and also establishes a link between the vital data measurement device 10 and the worker terminal 20 by means of a prescribed communication format (for example, Bluetooth (registered trademark)). The worker terminal 20 first prompts the worker P to select a measurer (i.e., the worker P) who is to measure the vital data (step S10). Next, the worker terminal 20 starts the measurement of vital data by the vital data measurement device 10 and stores the measured vital data (step S12; collection function), then displays the measured vital data on the display unit 25 (step S14). The worker terminal 20 compares the measured vital data with past vital data, and analyzes the health state of the worker P (step S16; health state determination function).

Next, the worker terminal 20 determines whether or not the health state of the worker P is within the normal range (or the vital data is within the normal range) based on the analysis results (step S18; health state determination function). Furthermore, if it is determined that the health state of the worker P is not within the normal range (or the vital data is not within the normal range) (NO in step S18), then the worker terminal 20 transmits to the industrial machine control device 50, via the network 30, the worker P's name (or worker ID), the vital data, the worker P's health state (outside the normal range), and that no questions are to be asked (step S26).

Meanwhile, if it is determined that there is a need to ask the worker P further questions relating to the health state and/or the safety checklist (YES in step S20), then the worker terminal 20 notifies the industrial machine control device 50, via the network 30, of the worker P's name (or worker ID), the vital data, the health state (within the normal range), and that questions are to be asked (step S24).

Meanwhile, if it is determined that the health state of the worker P is within the normal range (or the vital data is within the normal range) (YES in step S18), and there is no need to ask further questions (NO in step S20), then the worker terminal 20 notifies the industrial machine control device 50, via the network 30, of the worker P's name (or worker ID), the vital data, the health state (within the normal range), and that no questions are to be asked (step S22).

When the measurement of the vital data ends, the worker P moves to the location of the industrial machine operating panel 40 in order to operate the industrial machine 60. The industrial machine control device 50 prompts the worker P to select the worker P's name (or worker ID) (step S30 shown in FIG. 24), references the worker information storage unit 52 in accordance with the name (or worker ID) entered by the worker P, and on the basis of the vital data and the health state (within or outside the normal range) corresponding to the worker ID, received earlier from the worker terminal 20, displays a graphic representing the health state of the worker P on the display unit 57, as illustrated in one of FIGS. 14 to 19 (step S32).

Next, when the "Confirm" button on the screen 108 to the screen 113 is selected (touched) by the worker P, the industrial machine control device 50 determines, from the health state (within or outside the normal range) corresponding to the worker ID, received earlier from the worker terminal 20, whether or not the health state of the worker P is within the normal range (or the vital data is within the normal range) (step S34; control function). Furthermore, if it is determined that the health state of the worker P is not within the normal range (or the vital data is not within the normal range) (NO in step S34), then the industrial machine control device 50 alerts the manager terminal 70, via the network 30, of the worker P's name (or worker ID), the vital data, and the health state of the worker P (outside the normal range) (step S50).

When the manager terminal 70 is alerted, the manager determines, from the vital data and the health state (outside the normal range) of the worker P, whether the worker P can perform the work, whether the worker P should be replaced with another worker, and finally, whether or not the industrial machine 60 should be started. The industrial machine control device 50 is notified of the determination results (whether or not to allow startup of the industrial machine 60) from the manager terminal 70.

Next, the startup control unit 56 in the industrial machine control device 50 determines whether or not the manager terminal 70 has allowed startup of the industrial machine 60 (step S52). If startup of the industrial machine 60 has been allowed (YES in step S52), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if startup of the industrial machine 60 has not been allowed by the manager terminal 70 (NO in step S52), then the startup control unit 56 does not allow startup of the industrial machine 60 (step S48; control function). In other words, the startup control unit 56 turns off the startup of the industrial machine 60. Thereafter, the process ends. In this case, the worker P cannot perform work using the industrial machine 60.

Meanwhile, if the health state of the worker P is within the normal range (or the vital data is within the normal range) (YES in step S34), then the startup control unit 56 in the industrial machine control device 50 references the worker information storage unit 52 and determines whether or not questions relating to the health state and/or the safety checklist are to be asked (step S36). Furthermore, if the worker P is not to be asked questions relating to the health state and/or the safety checklist (NO in step S36), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if the health state of the worker P is within the normal range (or the vital data is within the normal range) and questions relating to the health state and/or the safety checklist are to be asked (YES in step S36), then the industrial machine control device 50 references the question information storage unit 54, reads out question information relating to the health state and/or the safety checklist in accordance with the department to which the worker P belongs, the skill level of the worker P, or the like, and displays the question information on the display unit 57 or outputs the question information as audio from the audio output unit 58 (step S38; health state question presentation function, cautionary question presentation function, and output function).

Thus, in addition to questions relating to the health of the worker P, the questions also include those relating to the safety checklist when starting work. The industrial machine control device 50 presents work-related cautions to the worker P in question form, determines whether or not there is a problem in the work starting conditions (safety) in addition to the health state of the worker P on the basis of the replies of the worker P to the questions, and controls whether or not to allow startup of the industrial machine 60 on the basis of the determination result. Thus, it is possible to ensure safety not only in terms of the health of the worker P, but also in terms of the work environment for performing work using the industrial machine 60.

The industrial machine control device 50 prompts the worker P to enter replies to the questions on the screen 114 (step S40), and the reply analysis unit 55 analyzes the replies to the questions relating to the health state and/or the safety checklist (step S42; health state reply determination function, cautionary reply determination function). Next, the reply analysis unit 55 in the industrial machine control device 50 determines whether or not there is a problem in the health state of the worker P and/or the safety, based on the results of the analysis of the replies to the questions relating to the health state (step S44; health state reply determination function, cautionary reply determination function). Furthermore, if it is determined that there are no problems in the health state of the worker P and/or the safety (NO in step S44), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if there is a problem in the health state of the worker P and/or the safety (YES in step S44), then the industrial machine control device 50 alerts the manager terminal 70, via the network 30, of the worker P's name (or worker ID), the vital data, the health state of the worker P (within the normal range), and the replies to the questions relating to the health state and/or the safety checklist (step S50).

When the manager terminal 70 is alerted, the manager determines, from the vital data of the worker P, the health state (within the normal range), and the replies to the questions relating to the health state and/or the safety checklist, whether the worker P can perform the work, whether the worker P should be replaced with another worker, and finally, whether or not the industrial machine 60 should be started. The industrial machine control device 50 is notified of the analysis results (whether or not to allow startup of the industrial machine 60) from the manager terminal 70.

The startup control unit 56 in the industrial machine control device 50 determines whether or not the manager terminal 70 has allowed startup of the industrial machine 60 (step S52), and if startup of the industrial machine 60 has been allowed (YES in step S52), then the startup control unit 56 allows startup of the industrial machine 60 (step S46; control function). In other words, the startup control unit 56 turns on the startup of the industrial machine 60. Thereafter, the process ends. In this case, the worker P can perform work using the industrial machine 60 as normal.

Meanwhile, if startup of the industrial machine 60 has not been allowed by the manager terminal 70 (NO in step S52), then the startup control unit 56 does not allow startup of the industrial machine 60 (step S48; control function). In other words, the startup control unit 56 turns off the startup of the industrial machine 60. Thereafter, the process ends. In this case, the worker P cannot perform work using the industrial machine 60.

According to the above-mentioned second embodiment, if the health state of the worker P is not within the normal range (or the vital data is not within the normal range), or the health state is within the normal range (or the vital data is within the normal range) but there is a problem in the replies to the questions relating to the health state and/or the safety checklist, then the manager terminal 70 used by the manager is alerted. And the manager determines whether or not to start the industrial machine 60. Thus, it is possible not only to control the startup of the industrial machine 60, but also to more flexibly perform more appropriate measures, such as determining whether the worker P is able to work, whether the worker P should be replaced with another worker, or the like.

C. Third Embodiment

Next, a third embodiment of the present invention will be explained.

Figure 25:
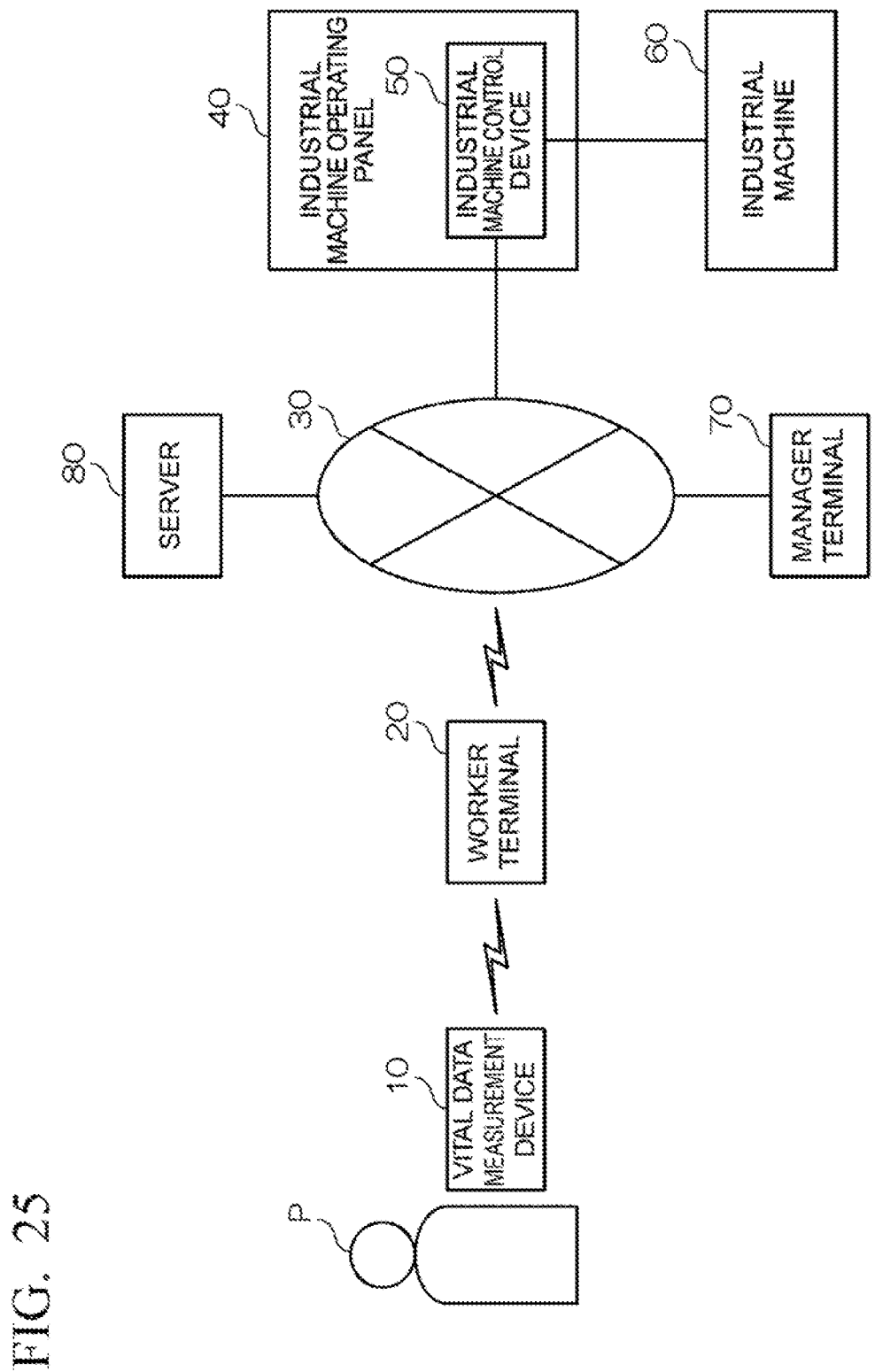
FIG. 25 is a block diagram illustrating the structure of an industrial machine startup control system 1 according to a third embodiment of the present invention.

FIG. 25 is a block diagram illustrating the structure of an industrial machine startup control system 1 according to the third embodiment of the present invention. The portions corresponding to those in FIG. 23 are assigned the same reference symbols and the descriptions thereof will be omitted.

In addition to the above-mentioned structure of the second embodiment, the present third embodiment is provided with a server 80 that is connected, via cable or wireless, to the network 30. The server (health state analysis device) 80, instead of the worker terminal 20, accumulates the vital data collected by the worker terminal 20 and analyzes the vital data, and notifies the worker terminal 20 of the analysis results (whether the health state is within or outside the normal range), and whether or not questions relating to the health state and/or the safety checklist are to be asked. The other actions are the same as those in the above-mentioned second embodiment, so the descriptions thereof will be omitted.

According to the above-mentioned third embodiment, instead of the worker terminal 20, the server 80 accumulates the vital data of the worker P, analyzes the vital data, and notifies the worker terminal 20 of the analysis results. Thus, it is possible to accumulate the vital data of the worker P and analyze the vital data without being affected by the processing power of the worker terminal 20 or the like.

D. Fourth Embodiment

Next, a fourth embodiment of the present invention will be explained.

Figure 26:
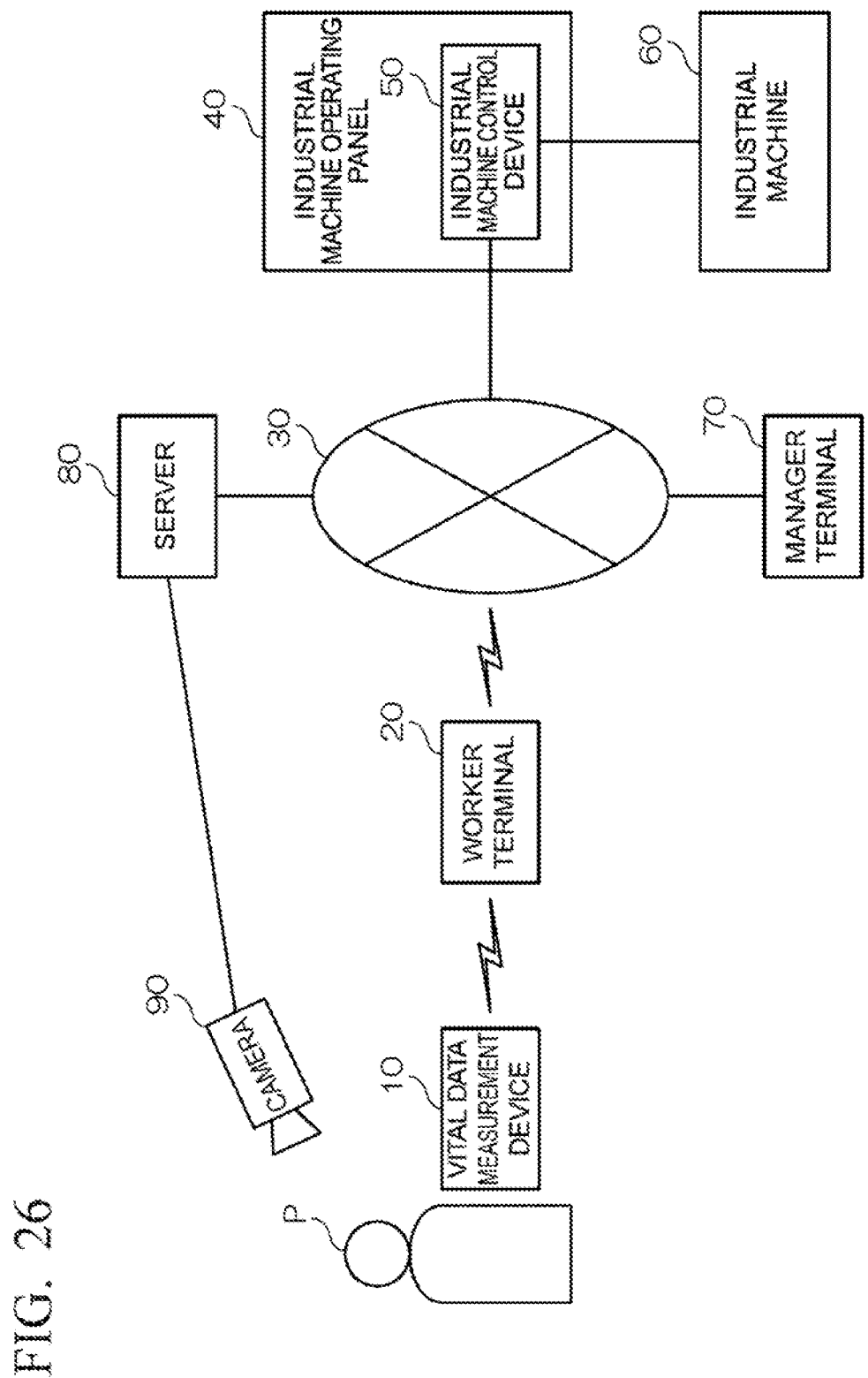
FIG. 26 is a block diagram illustrating the structure of an industrial machine startup control system 1 according to a fourth embodiment of the present invention.

FIG. 26 is a block diagram illustrating the structure of an industrial machine startup control system 1 according to the fourth embodiment of the present invention. The portions corresponding to those in FIG. 25 are assigned the same reference symbols and the descriptions thereof will be omitted.

In addition to the above-mentioned structure of the third embodiment, the present fourth embodiment is provided with a camera 90 that is connected to the server 80 via cable or wireless. The camera (imaging device) 90 captures images of the face of the worker P when the worker P is measuring the vital data. The server 80 analyzes changes in facial color, changes in facial expression, or the like from the images captured by the camera 90, and uses these changes as one of the parameters for determining the health state of the worker P. The camera 90 may be a camera that is mounted on the worker terminal 20.

Additionally, the camera 90 may be installed at a location for capturing images of the installation area of the industrial machine operating panel 40. In this case, the camera 90 captures images of the face of the worker P replying to the questions from the industrial machine control device 50. The server 80 analyzes changes in facial color, changes in facial expression, or the like from the images captured by the camera 90, and uses these analysis results as one of the parameters for determining the health state of the worker P.

Additionally, the camera 90 may be installed at a location from which it is possible to capture images of the worker P working with the industrial machine 60. In this case, the camera 90 continually (or intermittently) captures images of the worker P during the work. The server 80 analyzes the behavior of the worker P during the work from the images captured by the camera 90, and may use these analysis results as one of the parameters for determining the health state of the worker P or the conditions of the work environment.

According to the above-mentioned fourth embodiment, by using the camera 90, images of the face of the worker P are captured when the worker P measures the vital data, the behavior of the worker P during the work is analyzed from the captured images, and these analysis results are used as one of the parameters for determining the health state of the worker P. Thus, the health state of the worker P during the work can be more accurately determined.

Additionally, according to the above-mentioned fourth embodiment, by using the camera 90, images of the worker P are continually (or intermittently) captured during the work, and changes in facial color, changes in facial expression, or the like of the worker P are analyzed from the captured images and used as one of the parameters for determining the health state of the worker P. Thus, the health state of the worker P during the work can be more accurately determined.

In the above-mentioned first to fourth embodiments, the vital data of the worker P was only measured before the work was started. However, the invention is not limited thereto, and the vital data measurement device 10 may be in the form of a wearable device that can be continually worn, and the vital data of the worker P working with the industrial machine 60 may be taken continually (or intermittently) during the work. As a result thereof, the health state of the worker P can be analyzed during the work, and even if the worker P becomes ill during the work, startup of the industrial machine 60 may be allowed or not allowed by the industrial machine control device 50, such as by stopping the industrial machine 60 immediately or at an appropriate timing, thereby allowing appropriate measures to be quickly taken.

Additionally, in the above-mentioned second embodiment, if the health state of the worker P is not within the normal range (or the vital data is not within the normal range), or if the health state of the worker P is within the normal range (or the vital data is within the normal range) but it is determined that there is a problem in the health state and/or the safety checklist, then the manager terminal 70 was alerted by the industrial machine control device 50. As an alternative thereto, the manager terminal 70 may be alerted by the worker terminal 20.

The block diagram for this case is the same as that for the above-mentioned second embodiment, illustrated in FIG. 23.

In the flow chart shown in FIG. 4, if the health state of the worker P is not within the normal range (or the vital data is not within the normal range) (NO in step S18), then the worker terminal 20 transmits to the industrial machine control device 50, via the network 30, the worker P's name (or worker ID), the vital data, the health state (outside the normal range) of the worker P, and that no questions need to be asked (step S26), and simultaneously notifies the manager terminal 70 of the same information.

Additionally, the worker terminal 20 determines whether or not to further ask the worker P questions relating to the health state and/or the safety checklist by means of the industrial machine control device 50 (step S20), and if it is determined that further questions need to be asked (YES in step S20), then the worker terminal 20 notifies the industrial machine control device 50, via the network 30, of the worker P's name (or worker ID), the vital data, the health state (within the normal range), and that questions are to be asked (step S24), and simultaneously notifies the manager terminal 70 of the same information.

When the manager terminal 70 is alerted, the manager determines, from the vital data and the health state (outside the normal range) of the worker P, whether or not the worker P can perform the work, whether the worker P should be replaced with another worker, and finally, whether or not the industrial machine 60 should be started. The manager then notifies the industrial machine control device 50 of the determination results (whether or not to allow startup of the industrial machine 60) from the manager terminal 70.

In this case, in the flow chart for explaining the actions of the industrial machine control device 50 shown in FIG. 24, step S50 for alerting the manager terminal 70 is omitted.

In other words, in the industrial machine control device 50, if it is determined that the health state of the worker P is not within the normal range (or the vital data is not within the normal range) (corresponding to NO in step S34 in FIG. 24), then the startup control unit 56 in the industrial machine control device 50 determines whether or not the manager terminal 70 has allowed startup of the industrial machine 60 (corresponding to step S52). Furthermore, if startup of the industrial machine 60 has been allowed (corresponding to YES in step S52), the startup control unit 56 allows startup of the industrial machine 60 (corresponding to step S46; control function). In other words, the startup control unit 56 turns on the startup of the industrial machine 60. Thereafter, the process ends. In this case, the worker P can perform work using the industrial machine 60 as normal.

If the health state of the worker P is within the normal range (or the vital data is within the normal range) and questions relating to the health state and/or the safety checklist are to be asked (corresponding to YES in step S36), the same applies if, as a result of replying to the questions, there is a problem in the health state of the worker P and/or the safety (corresponding to YES in step S44).

When a server 80 is simultaneously provided in addition to the manager terminal 70, as in the above-mentioned third embodiment, the manager terminal 70 may be alerted by the server 80.

Additionally, in the above-mentioned fourth embodiment, a camera 90 is provided. However, this feature is not limited to the fourth embodiment, and may be similarly applied to the above-mentioned first to third embodiments as well.

REFERENCE SIGNS LIST

1 Industrial machine startup control system
10 Vital data measurement device
20 Worker terminal (health state analysis device)
21 Vital data acquisition unit
22 Vital data storage unit
23 Vital data analysis unit
24 Information transmission unit
25 Display unit
26 Operating unit (touch panel)
30 Network
40 Industrial machine operating panel
50 Industrial machine control device (startup control device)
51 Information reception unit
52 Worker information storage unit
53 Analysis result display control unit
54 Question information storage unit
55 Reply analysis unit
56 Startup control unit
57 Display unit
58 Audio output unit
59 Operating unit (touch panel)
60 Industrial machine
70 Manager terminal
80 Server (health state analysis device)
90 Camera (imaging device)
100 to 116 Screen
P Worker

The invention claimed is:

1. An industrial machine startup control system for controlling startup of an industrial machine, the industrial machine startup control system comprising:
a vital data measurement device configured to measure vital data of a worker;
a health state analysis device configured to (i) acquire the vital data of the worker measured by the vital data measurement device and (ii) determine a health state of the worker based on the vital data; and
a startup control device configured to control whether or not to allow startup of the industrial machine based on a determination result from the health state analysis device; wherein:
the health state analysis device is configured to (i) determine that the health state of the worker is normal if the vital data of the worker is in a prescribed range and (ii) determine, if the health state is normal, whether or not to ask the worker a question relating to the health state in accordance with a prescribed condition in the prescribed range and (iii) notify the startup control device of the determination result via a network, and
when the health state analysis device determines that the worker should be asked the question, the startup control device is configured to (i) present the worker with the question, (ii) determine whether or not there is a problem in the health state of the worker based on a reply from the worker responding to the question, and (iii) control whether or not to allow startup of the industrial machine based on the determination result and the reply.

2. The industrial machine startup control system as in claim 1, wherein:
the vital data measurement device is configured to measure the vital data of the worker at least before the worker performs work using the industrial machine.

3. The industrial machine startup control system as in claim 2, wherein:
the vital data measurement device is configured to measure the vital data of the worker during the work.

4. The industrial machine startup control system as in claim 1, wherein:
the health state analysis device is configured to determine that the health state of the worker is abnormal if the vital data of the worker is outside the prescribed range.

5. The industrial machine startup control system as in claim 1, wherein:
the health state analysis device is configured to (i) compare the vital data of the worker with past vital data of the worker and (ii) determine that the health state of the worker is abnormal if a change in the vital data satisfies a predetermined condition.

6. The industrial machine startup control system as in claim 1, further comprising:
a manager terminal configured to be used by a manager; wherein
if the health state of the worker is determined as being abnormal, the health state analysis device or the startup control device is configured to notify the manager terminal that the health state is abnormal; and
the startup control device is configured to control whether or not to allow startup of the industrial machine in accordance with a response from the manager terminal responding to the notification from the health state analysis device or the startup control device.

7. The industrial machine startup control system as in claim 1, wherein:
the health state analysis device is a specific worker terminal used by the worker.

8. The industrial machine startup control system as in claim 1, wherein:
the health state analysis device includes
a specific worker terminal that is configured to (i) be used by the worker and (ii) acquire the vital data of the worker measured by the vital data measurement device; and
a server that is configured to (i) determine the health state of the worker based on the vital data acquired by the specific worker terminal and (ii) notify the specific worker terminal of the determination result.

9. The industrial machine startup control system as in claim 8, further comprising:
an imaging device that is configured to capture an image of the worker; wherein
the server is configured to (i) analyze the image that has been captured by the imaging device and (ii) determine the health state of the worker based on at least a facial expression and/or a facial color of the worker in addition to the vital data.

10. The industrial machine startup control system as in claim 9, wherein:
the imaging device is configured to capture an image of behavior of the worker during the work; and
the server is configured to (i) analyze the captured image that has been captured by the imaging device and (ii) determine the health state of the worker based on the behavior of the worker during the work.

11. The industrial machine startup control system as in claim 1, wherein the vital data includes at least blood pressure, body temperature, and pulse.

12. The industrial machine startup control system as in claim 1, wherein:
the startup control device is configured to (i) present a work-related caution to the worker in question form, (ii) determine whether or not there is a problem in work starting conditions based on a reply to the work-related question, and (iii) control whether or not to allow startup of the industrial machine based on the reply.

13. The industrial machine startup control system as in claim 12, wherein:
the startup control device includes an audio output unit that plays and outputs, as audio, the inquiry relating to the health state and the work-related caution.

14. A startup control method for controlling startup of an industrial machine, the startup control method comprising:
a step of measuring vital data of a worker by using a vital data measurement device;
a step of determining a health state of the worker, by using a health state analysis device, based on the vital data of the worker measured by the vital data measurement device; and
a step of controlling whether or not to allow startup of the industrial machine, by using a startup control device, based on a determination result from the health state analysis device, wherein:
the step of determining a health state of the worker includes (i) determining that the health state of the worker is normal if the vital data of the worker is in a prescribed range, (ii) determining, if the health state is normal, whether or not to ask the worker a question relating to the health state in accordance with a prescribed condition in the prescribed range, and (iii) notifying the startup control device of the determination result via a network; and
the step of controlling whether or not to allow startup of the industrial machine includes, when the health state analysis device determines that the worker should be asked the question, (i) presenting the worker with the question, (ii) determining whether or not there is a problem in the health state of the worker based on a reply from the worker responding to the question, and (iii) controlling whether or not to allow startup of the industrial machine based on the determination result and the reply.

* * * * *